US012758095B2

(12) United States Patent
Wang et al.

(10) Patent No.: US 12,758,095 B2
(45) Date of Patent: Oct. 13, 2026

(54) TECHNIQUES FOR AUTOMATICALLY SEGMENTING OCULAR IMAGERY AND PREDICTING PROGRESSION OF AGE-RELATED MACULAR DEGENERATION

(71) Applicant: University of Washington, Seattle, WA (US)

(72) Inventors: Ruikang K. Wang, Seattle, WA (US); Zhongdi Chu, Seattle, WA (US)

(73) Assignee: University of Washington, Seattle, WA (US)

( * ) Notice: Subject to any disclaimer, the term of this patent is extended or adjusted under 35 U.S.C. 154(b) by 366 days.

(21) Appl. No.: 18/558,121

(22) PCT Filed: Apr. 29, 2022

(86) PCT No.: PCT/US2022/027002

§ 371 (c)(1),
(2) Date: Oct. 30, 2023

(87) PCT Pub. No.: WO2022/232555

PCT Pub. Date: Nov. 3, 2022

(65) Prior Publication Data

US 2024/0206727 A1 Jun. 27, 2024

Related U.S. Application Data

(60) Provisional application No. 63/182,328, filed on Apr. 30, 2021.

(51) Int. Cl.

*G06K 9/00* (2022.01)
*A61B 3/10* (2006.01)

(Continued)

(52) U.S. Cl.

CPC ............ *A61B 3/102* (2013.01); *A61B 3/1005* (2013.01); *A61B 3/107* (2013.01); *G06T 7/0012* (2013.01);

(Continued)

(58) Field of Classification Search

None

See application file for complete search history.

(56) References Cited

U.S. PATENT DOCUMENTS 10,117,568 B2 * 11/2018 Reisman ................ A61B 3/102
10,433,723 B2 10/2019 Naba (Continued)

FOREIGN PATENT DOCUMENTS

CN 112715484 A 4/2021
JP 2021100572 A 7/2021

(Continued)

OTHER PUBLICATIONS

Paul F. Stetson, et al., "OCT Minimum Intensity as a Predictor of Geographic Atrophy Enlargement"; Investigative Ophthalmology & Visual Science; The Association for Research in Vision and Ophthalmology, Inc.; Published Feb. 2014/vol. 55/No. 2., pp. 792-800. (Year: 2014).*

(Continued)

*Primary Examiner* — Wei Wen Yang

(74) *Attorney, Agent, or Firm* — Christensen O'Connor Johnson Kindness PLLC

(57) ABSTRACT

In some embodiments, a computer-implemented method of automatically predicting progression of age-related macular degeneration is provided. An image analysis computing system receives optical coherence tomography data (OCT data). The image analysis computing system determines an optical attenuation coefficient for each pixel of the OCT data to create optical attenuation coefficient data (OAC data)

(Continued)

corresponding to the OCT data. The image analysis computing system determines an area exhibiting geographic atrophy based on at least one of the OCT data and the OAC data. The image analysis computing system measures one or more attributes within an adjacent area that is adjacent to the area exhibiting geographic atrophy, and the image analysis computing system determines a predicted enlargement rate based on the one or more attributes within the adjacent area.

16 Claims, 25 Drawing Sheets

(51) Int. Cl.

| | |
|---|---|
| ***A61B 3/107*** | (2006.01) |
| ***G06T 7/00*** | (2017.01) |
| ***G16H 30/40*** | (2018.01) |
| ***G16H 50/20*** | (2018.01) |

(52) U.S. Cl.
CPC ............. *G16H 30/40* (2018.01); *G16H 50/20* (2018.01); *G06T 2207/10101* (2013.01); *G06T 2207/20081* (2013.01); *G06T 2207/30041* (2013.01)

(56) References Cited

U.S. PATENT DOCUMENTS

| | | | | |
|---|---|---|---|---|
| 2016/0174830 | A1 | 6/2016 | Rubin | |
| 2016/0206190 | A1 | 7/2016 | Reisman | |
| 2017/0022562 | A1 | 1/2017 | Golestaneh | |
| 2017/0119243 | A1 | 5/2017 | Irvine | |
| 2018/0182082 | A1 | 6/2018 | Jia | |
| 2021/0110537 | A1 | 4/2021 | Wakeford | |
| 2021/0295508 | A1 | 9/2021 | Shiba | |
| 2021/0319556 | A1 | 10/2021 | Chauhan | |
| 2021/0357696 | A1 | 11/2021 | Peng | |
| 2023/0140881 | A1* | 5/2023 | De Sisternes .......... | A61B 3/102 382/130 |

FOREIGN PATENT DOCUMENTS

| | | | | |
|---|---|---|---|---|
| WO | 2009035564 A1 | 3/2009 | | |
| WO | 2015168157 A1 | 11/2015 | | |
| WO | 2021120587 A1 | 6/2021 | | |
| WO | 2021151077 A1 | 7/2021 | | |
| WO | WO-2022120044 A1 * | 6/2022 | ........... | G06T 7/0012 |

OTHER PUBLICATIONS

S. E. Chung, S. W. Kang, J. H. Lee, and Y. T. Kim, "Choroidal Thickness in Polypoidal Choroidal Vasculopathy and Exudative Age-Related Macular Degeneration," Ophthalmology 118(5), 840-845 (2011).

I. Maruko, T. Iida, Y. Sugano, A. Ojima, M. Ogasawara, and R. F. Spaide, "Subfoveal Choroidal Thickness after Treatment of Central Serous Chorioretinopathy," Ophthalmology 117(9), 1792-1799 (2010).

Y. Imamura, T. Fujiwara, R. Margolis, and R. F. Spaide, "Enhanced Depth Imaging Optical Coherence Tomography of the Choroid in Central Serous Chorioretinopathy," Retina 29(10), 1469-1473 (2009).

I. Maruko, T. Iida, Y. Sugano, S. Go, and T. Sekiryu, "Subfoveal Choroidal Thickness in Papillitis Type of Vogt-Koyanagi-Harada Disease and Idiopathic Optic Neuritis," Retina 36(5), 992-999 (2016).

R. P. Nunes, R. Goldhardt, C. A. de Amorim Garcia Filho, M. R. Thorell, A. M. Abbey, A. E. Kuriyan, Y. S. Modi, M. Shah, Z. Yehoshua, G. Gregori, W. Feuer, and P. J. Rosenfeld, "Spectral-Domain Optical Coherence Tomography Measurements of Choroidal Thickness and Outer Retinal Disruption in Macular Telangiectasia Type 2," Ophthalmic Surg. Lasers Imaging Retina 46(2), 162-170 (2015).

H. Ohsugi, Y. Ikuno, K. Oshima, and H. Tabuchi, "3-D Choroidal Thickness Maps from EDI-OCT in Highly Myopic Eyes," Optom. Vis. Sci. 90(6), 599-606 (2013).

S. Kase, H. Endo, M. Yokoi, M. Kotani, S. Katsuta, M. Takahashi, and M. Kase, "Choroidal thickness in diabetic retinopathy in relation to long-term systemic treatments for diabetes mellitus," Eur. J. Ophthalmol. 26(2), 158-162 (2016).

M. R. Thorell, R. Goldhardt, R. P. Nunes, C. A. de Amorim Garcia Filho, A. M. Abbey, A. E. Kuriyan, Y. S. Modi, G. Gregori, Z. Yehoshua, W. Feuer, S. Sadda, and P. J. Rosenfeld, "Association Between Subfoveal Choroidal Thickness, Reticular Pseudodrusen, and Geographic Atrophy in Age-Related Macular Degeneration," Ophthalmic Surg. Lasers Imaging Retina 46(5), 513-521 (2015).

A. R. Miller, L. Roisman, Q. Zhang, F. Zheng, J. Rafael de Oliveira Dias, Z. Yehoshua, K. B. Schaal, W. Feuer, G. Gregori, Z. Chu, C. L. Chen, S. Kubach, L. An, P. F. Stetson, M. K. Durbin, R. K. K. Wang, and P. J. Rosenfeld, "Comparison Between Spectral-Domain and Swept-Source Optical Coherence Tomography Angiographic Imaging of Choroidal Neovascularization," Invest. Ophthalmol. Vis. Sci. 58(3), 1499-1505 (2017).

A. I. Dastiridou, E. Bousquet, L. Kuehlewein, T. Tepelus, D. Monnet, S. Salah, A. Brezin, and S. R. Sadda, "Choroidal Imaging with Swept-Source Optical Coherence Tomography in Patients with Birdshot Chorioretinopathy: Choroidal Reflectivity and Thickness," Ophthalmology 124(8), 1186-1195 (2017).

R. Margolis and R. F. Spaide, "A Pilot Study of Enhanced Depth Imaging Optical Coherence Tomography of the Choroid in Normal Eyes," Am. J. Ophthalmol. 147(5), 811-815 (2009).

R. F. Spaide, H. Koizumi, and M. C. Pozzoni, "Enhanced depth imaging spectral-domain optical coherence tomography," Am. J. Ophthalmol. 146(4), 496-500 (2008).

K. K. Vupparaboina, K. K. Dansingani, A. Goud, M. A. Rasheed, F. Jawed, S. Jana, A. Richhariya, B. K. Freund, and J. Chhablani, "Quantitative shadow compensated optical coherence tomography of choroidal vasculature," Sci. Rep. 8, 6461, 1-9 (2018).

L. Zhang, K. Lee, M. Niemeijer, R. F. Mullins, M. Sonka, and M. D. Abramoff, "Automated Segmentation of the Choroid from Clinical SD-OCT," Invest. Ophthalmol. Vis. Sci. 53(12), 7510-7519 (2012).

V. Kajic, M. Esmaeelpour, C. Glittenberg, M. F. Kraus, J. Honegger, R. Othara, S. Binder, J. G. Fujimoto, and W. Drexler, "Automated three-dimensional choroidal vessel segmentation of 3D 1060 nm OCT retinal data," Biomed. Opt. Express 4(1), 134-150 (2013).

G. Yiu, P. Pecen, N. Sarin, S. J. Chiu, S. Farsiu, P. Mruthyunjaya, and C. A. Toth, "Characterization of the Choroid-Scleral Junction and Suprachoroidal Layer in Healthy Individuals on Enhanced-Depth Imaging Optical Coherence Tomography," JAMA Ophthalmol. 132(2), 174-181 (2014).

L. Beaton, J. Mazzaferri, F. Lalonde, M. Hidalgo-Aguirre, D. Descovich, M. R. Lesk, and S. Costantino, "Non-invasive measurement of choroidal vol. change and ocular rigidity through automated segmentation of high-speed OCT imaging," Biomed. Opt. Express 6(5), 1694-1706 (2015).

Q. Chen, W. Fan, S. Niu, J. Shi, H. Shen, and S. Yuan, "Automated choroid segmentation based on gradual intensity distance in HD-OCT images," Opt. Express 23(7), 8974-8994 (2015).

L. Duan, Y. J. Hong, and Y. Yasuno, "Automated segmentation and characterization of choroidal vessels in high-penetration optical coherence tomography," Opt. Express 21(13), 15787-15808 (2013).

J. Mazzaferri, L. Beaton, G. Hounye, D. N. Sayah, and S. Costantino, "Open-source algorithm for automatic choroid segmentation of OCT volume reconstructions," Sci. Rep. 7, 42112 (2017).

D. Alonso-Caneiro, S. A. Read, and M. J. Collins, "Automatic segmentation of choroidal thickness in optical coherence tomography," Biomed. Opt. Express 4(12), 2795-2812 (2013).

R. K. K. Wang, "Signal degradation by coherence tomography multiple scattering in optical of dense tissue: a Monte Carlo study towards optical clearing of biotissues," Phys. Med. Biol. 47, 2281-2299 (2002).

C. Xu, J. M. Schmitt, S. G. Carlier, and R. Virmani, "Characterization of atherosclerosis plaques by measuring both backscattering and attenuation coefficients in optical coherence tomography," J. Biomed. Opt. 13(3), 034003, pp. 1-8 (2008).

(56) References Cited

OTHER PUBLICATIONS

L. Scolaro, R. A. McLaughlin, B. R. Klyen, B. A. Wood, P. D. Robbins, C. M. Saunders, S. L. Jacques, and D. D. Sampson, "Parametric imaging of the local attenuation coefficient in human axillary lymph nodes assessed using optical coherence tomography," Biomed. Opt. Express 3(2), 366-379 (2012).

E. C. C. Cauberg, D. M. de Bruin, D. J. Faber, T. M. de Reijke, M. Visser, J. J. M. C. H. de la Rosette, and T. G. van Leeuwen, "Quantitative measurement of attenuation coefficients of bladder biopsies using optical coherence tomography for grading urothelial carcinoma of the bladder," J. Biomed. Opt. 15(6), 066013, pp. 1-6 (2010).

U. Baran, Y. Li, and R. K. Wang, "In vivo tissue injury mapping using optical coherence tomography based methods," Appl. Opt. 54(21), 6448-6453 (2015).

U. Baran, W. Zhu, W. J. Choi, M. Omori, W. Zhang, N. J. Alkayed, and R. K. K. Wang, "Automated segmentation and enhancement of optical coherence tomography-acquired images of rodent brain," J. Neurosci. Methods 270, 132-137 (2016).

U. Baran, W. Qin, X. L. Qi, G. Kalkan, and R. K. Wang, "OCT-based label-free in vivo lymphangiography within human skin and areola," Sci. Rep. 6, 21122, pp. 1-8 (2016).

M. J. A. Girard, N. G. Strouthidis, C. R. Ethier, and J. M. Mari, "Shadow Removal and Contrast Enhancement in Optical Coherence Tomography Images of the Human Optic Nerve Head," Invest. Ophthalmol. Vis. Sci. 52(10), 7738-7748 (2011).

Chen, C.L. and Ruikang K. Wang, "Optical coherence tomography based angiography [Invited]," Biomedical Optical Express; vol. 8, No. 2, Feb. 1, 2017, pp. 1056-1082. <https://opg.optica.org/boe/fulltext.cfm uri=boe-8-2-1056&id=357629>.

P. H. Tomlins and R. K. Wang, "Theory, developments and applications of optical coherence tomography," J. Phys. D Appl. Phys. 38(15), 2519-2535 (2005).

K. A. Vermeer, J. Mo, J. J. A. Weda, H. G. Lemij, and J. F. de Boer, "Depth-resolved model-based reconstruction of attenuation coefficients in optical coherence tomography," Biomed. Opt. Express 5(1), 322-337 (2014).

P. H. C. Eilers, I. D. Currie, and M. Durban, "Fast and compact smoothing on large multidimensional grids," Comput. Stat. Data Anal. 50(1), 61-76 (2006).

S. M. Pizer, E. P. Amburn, J. D. Austin, R. Cromartie, A. Geselowitz, T. Greer, B. Terhaarromeny, J. B. Zimmerman, and K. Zuiderveld, "Adaptive Histogram Equalization and Its Variations," Comput Vision Graph 39(3), 355-368 (1987).

L. Zhang, G. H. S. Buitendijk, K. Lee, M. Sonka, H. Springelkamp, A. Hofman, J. R. Vingerling, R. F. Mullins, C. C. W. Klaver, and M. D. Abramoff, "Validity of Automated Choroidal Segmentation in SS-OCT and SD-OCT," Invest. Ophthalmol. Vis. Sci. 56(5), 3202-3211 (2015).

Q. Q. Zhang, C. S. Lee, J. Chao, C. L. Chen, T. Zhang, U. Sharma, A. Q. Zhang, J. Liu, K. Rezaei, K. L. Pepple, R. Munsen, J. Kinyoun, M. Johnstone, R. N. Van Gelder, and R. K. K. Wang, "Wide-field optical coherence tomography based microangiography for retinal imaging," Sci. Rep. 6, 22017, pp. 1-10 (2016).

Thulliez, M., Zhang, Q., Shi, Y., Zhou, H., Chu, Z., de Sisternes, L., Durbin, M. K., Feuer, W., Gregori, G., Wang, R. K., & Rosenfeld, P. J. (2019); "Correlations between Choriocapillaris Flow Deficits around Geographic Atrophy and Enlargement Rates Based on Swept-Source OCT Imaging," Ophthalmology. Retina, 3(6), 478-488; https://doi.org/10.1016/j.oret.2019.01.024.

Ho BS, BA, Joseph et al., "Documentation of Intraretinal Retinal Pigment Epithelium Migration via High-Speed Ultrahigh-Resolution Optical Coherence Tomography," Elsevier: Ophthalmology vol. 118, Issue 4, Apr. 2011, pp. 687-693.

Knott, E. J. et al., "Spatial correlation of mouse photoreceptor-RPE thickness between SD OCT and histology," Elsevier: Experimntal Eye Research vol. 92, Issue 2, Feb. 2011, pp. 155-160.

Yoshiaki Yasuno, Masahiro Miura, Keisuke Kawana, Shuichi Makita, Masaki Sato, Fumiki Okamoto, Masahiro Yamanari, Takuya Iwasaki, Toyohiko Yatagai, Tetsuro Oshika; "Visualization of Sub-retinal Pigment Epithelium Morphologies of Exudative Macular Diseases by High-Penetration Optical Coherence Tomography." Invest. Ophthalmol. Vis. Sci. 2009;50(1):405-413. https://doi.org/10.1167/iovs.08-2272.

Koenraad A. Vermeer, Josine van der Schoot, Hans G. Lemij, Johannes F. de Boer; "RPE-Normalized RNFL Attenuation Coefficient Maps Derived from Volumetric OCT Imaging for Glaucoma Assessment." Invest. Ophthalmol. Vis. Sci. 2012;53(10):6102-6108. https://doi.org/10.1167/iovs.12-9933.

Kurmann, T., Yu, S., Márquez-Neila, P. et al. "Expert-level Automated Biomarker Identification in Optical Coherence Tomography Scans." Sci Rep 9, 13605, pp. 1-9 (2019). https://doi.org/10.1038/s41598-019-49740-7.

Keidel, L. et al., "Establishing an objective biomarker for corneal cystinosis using a threshold-based Spectral domain optical coherence tomography imaging algorithm," Acta Ophthalmologica vol. 99, Issue 2, Mar. 2021, pp. e189-e195.

Leopold, H. A. et al., "Chapter 12—Deep learning for ophthalmology using optical coherence tomography," Science Direct: State of the Art in Neural Networks and their Applications, vol. 1, 2021, pp. 239-269.

Mbing Hu, Chen Tang, Min Xu, and Zhenkun Lei, "Selective retinex enhancement based on the clustering algorithm and block-matching 3D for optical coherence tomography images," Appl. Opt. 58, 9861-9869 (2019).

Folio LS, Wollstein G, Ishikawa H, et al., "Variation in optical coherence tomography signal quality as an indicator of retinal nerve fibre layer segmentation error." British Journal of Ophthalmology 2012;96:514-518.

Maximilian W.M. Wintergerst, Thomas Schultz, Johannes Birtel, Alexander K. Schuster, Norbert Pfeiffer, Steffen Schmitz-Valckenberg, Frank G. Holz, Robert P. Finger; "Algorithms for the Automated Analysis of Age-Related Macular Degeneration Biomarkers on Optical Coherence Tomography: A Systematic Review." Trans. Vis. Sci. Tech. 2017;6(4):10. pp. 1-20. https://doi.org/10.1167/tvst.6.4.10.

N. Bhargava, P. Trivedi, A. Toshniwal and H. Swarnkar, "Iterative Region Merging and Object Retrieval Method Using Mean Shift Segmentation and Flood Fill Algorithm," 2013 Third International Conference on Advances in Computing and Communications, Cochin, India, 2013, pp. 157-160, doi: 10.1109/ICACC.2013.100.

Keane MRCOphth MSc, Pearse A. et al., "Evaluation of Age-related Macular Degeneration With Optical Coherence Tomography," Elsevier: Survey of Ophthalmology, vol. 57, Issue 5, Sep.-Oct. 2012, pp. 389-414.

Lee Md C. S. et al, "Deep Learning Is Effective for Classifying Normal versus Age-Related Macular Degeneration OCT Images," Elsevier: Ophthalmology Retina vol. 1, Issue 4, Jul.-Aug. 2017, pp. 322-327.

Abbey, A. M. et al., "Optical Coherence Tomography Measurements of Choroidal Thickness in Healthy Eyes: Correlation With Age and Axial Length," Ophthalmic Surgery, Lasers & Imaging Retina 2015;46: 18-24.

Agarwal, A. et al., "Choroidal Structural Changes in Tubercular Multifocal Serpiginoid Choroiditis," (2018) Choroidal Structural Changes in Tubercular Multifocal Serpiginoid Choroiditis, Ocular Immunology and Inflammation, 26:6, 838-844, DOI: 10.1080/09273948.2017.1370650.

Nickla DL, Wallman J. The multifunctional choroid. ProgRetin Eye Res. 2010;29:144-168.

Linsenmeier RA, Padnick-Silver L. Metabolic dependence of photoreceptors on the choroid in the normal and detached retina. Invest Ophthalmol Vis Sci. 2000;41:3117-3123.

Hayreh SS. Blood supply of the optic nerve head and its role in optic atrophy, glaucoma, and oedema of the optic disc. Br J Ophthalmol. 1969;53:721-748.

Parver LM, Auker C, Carpenter DO. Choroidal blood-flow as a heat dissipating mechanism in the macula. Am J Ophthalmol. 1980;89:641-646.

Yannuzzi LA, Rohrer KT, Tindel LJ, et al. Fluorescein angiography complication survey. Ophthalmology. 1986;93:611-617.

Bloome MA. Fluorescein angiography: risks. Vision research. 1980;20:1083-1097.

(56) References Cited

OTHER PUBLICATIONS

Mrejen S, Spaide RF. Optical coherence tomography: Imaging of the choroid and beyond. Surv Ophthalmol. 2013;58:387-429.
Laviers H, Zambarakji H. Enhanced depth imaging-OCT of the choroid: a review of the current literature. Graefes Arch Clin Exp Ophthalmol. 2014;252:1871-1883.
Agrawal R, Gupta P, Tan KA, et al. Choroidal vascularity index as a measure of vascular status of the choroid: Measurements in healthy eyes from a population-based study. SciRep. 2016;6:21090.
Choma MA, Sarunic MV, Yang CH, Izatt JA. Sensitivity advantage of swept source and Fourier domain optical coherence tomography. Opt Express. 2003;11:2183-2189.
Yasin Alibhai A, Or C, Witkin AJ. Swept source optical coherence tomography: a review. Curr Ophthalmol Rep.2018;6:7-16.
Lavinsky F, Lavinsky D. Novel perspectives on swept-source optical coherence tomography. Int J Retina Vitreous. 2016;2:25; pp. 1-11.
Singh SR, Invernizzi A, Rasheed MA, et al. Wide-field choroidal vascularity in healthy eyes. Am J Ophthalmol.2018;193:100-105.
Ruiz-Medrano J, Ruiz-Moreno JM, Goud A, et al. Age-related changes in choroidal vascular density of healthy subjects based on image binarization of swept-source optical coherence tomography. Retina. 2018;38:508-515.
Sonoda S, Sakamoto T, Kakiuchi N, et al. Semi-automated software to measure luminal and stromal areas of choroid in optical coherence tomographic images. Jpn J Ophthalmol.2018;62:179-185.
Sonoda S, Sakamoto T, Yamashita T, et al. Luminal and stromal areas of choroid determined by binarization method of optical coherence tomographic images. Am J Ophthalmol.2015;159:1123-1131.
Hirata M, Tsujikawa A, Matsumoto A, et al. Macular choroidal thickness and volume in normal subjects measured by swept-source optical coherence tomography. Invest Ophthalmol Vis Sci. 2011;52:4971-4978.
Jirarattanasopa P, Ooto S, Tsujikawa A, et al. Assessment of macular choroidal thickness by optical coherence tomography and angiographic changes in central serous chorioretinopathy. Ophthalmology. 2012;119:1666-1678.
Wang JC, Lains I, Providencia J, et al. Diabetic choroidopathy: choroidal vascular density and volume in diabetic retinopathy with swept-source optical coherence tomography. Am J Ophthalmol. 2017;184:75-83.
Zheng F, Gregori G, Schaal KB, et al. Choroidal thickness and choroidal vessel density in nonexudative age-related macular degeneration using swept-source optical coherence tomography imaging. Invest Ophthalmol Vis Sci. 2016;57:6256-6264.
Zhou H, Chu Z, Zhang Q, et al. Attenuation correction assisted automatic segmentation for assessing choroidal thickness and vasculature with swept-source OCT. Biomed Opt Express.2018;9:6067-6080.
An L, Wang RKK. In vivo volumetric imaging of vascular perfusion within human retina and choroids with optical micro-angiography. Opt Express. 2008; 16:11438-11452.
Kashani AH, Chen CL, Gahm JK, et al. Optical coherence tomography angiography: a comprehensive review of current methods and clinical applications. Prog Retin Eye Res.2017;60:66-100.
Kirby MA, Li C, Choi WJ, et al. Why choroid vessels appear dark in clinical OCT images. Proceedings of the Society of Photo-optical Instrumentation Engineers, Ophthalmic Technologies XXVIII. Bellingham, WA: Society of Photo-optical Instrumentation Engineers; 2018:1047428; pp. 1-5.
Wang RKK, Kirby M, Li CX, et al. An explanation for why choroidal blood vessels appear dark on clinical OCT images. Invest Ophthalmol Vis Sci. 2017;58: 4754; pp. 1-3.
Claudon M, Tranquart F, Evans DH, et al. Advances in ultrasound. Eur Radiol. 2002;12:7-18.
Zheng F, Zhang QQ, Shi YY, et al. Age-dependent changes in the macular choriocapillaris of normal eyes imaged with swept-source optical coherence tomography angiography. Am J Ophthalmol. 2019;200:110-122.
Ogawa Y, Maruko I, Koizumi H, Iida T. Quantification of choroidal vasculature by high-quality structure en face swept-source optical coherence tomography images in eyes with central serous chorioretinopathy [published online ahead of print Dec. 2013]. Retina. 2018; pp. 529-536.
Agrawal R, Wei X, Goud A, et al. Influence of scanning area on choroidal vascularity index measurement using optical coherence tomography. Acta Ophthalmol. 2017;95; pp. e770-e775.
Ambiya V, Goud A, Rasheed MA, et al. Retinal and choroidal changes in steroid-associated central serous chorioretinopathy. Int J Retina Vitreous. 2018;4:11; pp. 1-7.
Tan KA, Laude A, Yip V, et al. Choroidal vascularity index a novel optical coherence tomography parameter for disease monitoring in diabetes mellitus? Acta Ophthalmol. 2016;94(7); pp. e612-e616.
Kim M, Ha MJ, Choi SY, Park YH. Choroidal vascularity index in type-2 diabetes analyzed by swept-source optical coherence tomography. Sci Rep. 2018;8:70; pp. 1-8.
Agrawal R, Li LKH, Nakhate V, et al. Choroidal vascularity index in Vogt-Koyanagi-Harada disease: an EDI-OCT derived tool for monitoring disease progression. Transl Vis Sci Techn.2016;5:7; pp. 1-9.
Gallego-Pinazo R, Dolz-Marco R, Gomez-Ulla F, et al. Pachychoroid diseases of the macula. Med Hypothesis Discov Innov Ophthalmol. 2014;3:111-115.
Zhang QQ, Shi YY, Zhou H, et al. Accurate estimation of choriocapillaris flow deficits beyond normal intercapillary spacing with swept source OCT angiography. Quant Imaging Med Surg. 2018;8:658-666.
Zhang QQ, Zheng F, Motulsky EH, et al. A novel strategy for quantifying choriocapillaris flow voids using swept-source OCT angiography. Invest Ophthalmol Vis Sci. 2018;59:203-211.
Chu ZD, Zhou H, Cheng YX, et al. Improving visualization and quantitative assessment of choriocapillaris with swept source OCTA through registration and averaging applicable to clinical systems. Sci Rep. 2018;8:16826; pp. 1-13.
Zhang QQ, Lee CS, Chao J, et al. Wide-field optical coherence tomography based microangiography for retinal imaging. SciRep. 2016;6:22017; pp. 1-10.
Huynh E, Chandrasekera E, Bukowska D, et al. Past, present, and future concepts of the choroidal scleral interface morphology on optical coherence tomography. Asia Pac J Ophthalmol (Phila). 2017;6:94-103.
Vuong VS, Moisseiev E, Cunefare D, et al. Repeatability of choroidal thickness measurements on enhanced depth imaging optical coherence tomography using different posterior boundaries. Am J Ophthalmol. 2016;169:104-112.
Kim M, Kim RY, Kim JY, Park YH. Correlation of systemic arterial stiffness with changes in retinal and choroidal micro-vasculature in type 2 diabetes. Sci Rep. 2019;9:1401; pp. 1-9.
Tan R, Agrawal R, Taduru S, et al. Choroidal vascularity index in retinitis pigmentosa: an OCT study. Ophthalmic Surg Lasers Imaging Retina. 2018;49:191-197.
Ratra D, Tan R, Jaishankar D, et al. Choroidal structural changes and vascularity index in stargardt disease on swept source optical coherence tomography. Retina. 2018;38:2395-2400.
Invernizzi A, Benatti E, Cozzi M, et al. Choroidal structural changes correlate with neovascular activity in neovascular age related macular degeneration. Invest Ophthalmol Vis Sci.2018;59:3836-3841.
Ng WY, Ting DSW, Agrawal R, et al. Choroidal structural changes in myopic choroidal neovascularization after treatment with antivascular endothelial growth factor over 1 year. Invest Ophthalmol Vis Sci. 2016;57:4933-4939.
Ting DSW, Yanagi Y, Agrawal R, et al. Choroidal remodeling in age-related macular degeneration and polypoidal choroidal vasculopathy: a 12-month prospective study. Sci Rep. 2017;7:7868.
Knighton RW, Gregori G. The shape of the ganglion cell plus inner plexiform layers of the normal human macula. Invest Ophthalmol Vis Sci. 2012;53:7412-7420.
P. Haas, M. Esmaeelpour, S. Ansari-Shahrezaei, W. Drexler, and S. Binder, "Choroidal thickness in patients with reticular pseudodrusen using 3D 1060-nm OCT maps," Invest. Ophthalmol. Vis. Sci. 55(4), Apr. 2014; 2674-2681.

(56) References Cited

OTHER PUBLICATIONS

Sadda Md, S. R. et al., "Consensus Definition for Atrophy Associated with Age-Related Macular Degeneration on OCT: Classification of Atrophy Report 3," Elsevier: Ophthalmology vol. 125, Issue 4, Apr. 2018, pp. 537-548.
Jia PhD, Y. et al., "Quantitative Optical Coherence Tomography Angiography of Choroidal Neovascularization in Age-Related Macular Degeneration," Elsevier: Ophthalmology vol. 121, Issue 7, Jul. 2014, pp. 1435-1444.
Binder, S. et al., "Transplantation of the RPE in AMD," Progress in Retinal and Eye Research vol. 26, Issue 5, Sep. 2007, pp. 516-554.
Feher, J. et al., "Mitochondrial alterations of retinal pigment epithelium in age-related macular degeneration," Elsevier: Neurobiology of Aging vol. 27, Issue 7, Jul. 2006, pp. 983-993.
Brown, E. E. et al., "Mitochondrial oxidative stress in the retinal pigment epithelium (RPE) led to metabolic dysfunction in both the RPE and retinal photoreceptors," Elsevier: Redox Biology vol. 24, Jun. 2019, 101201, pp. 1-11.
Eaton-Rosen, Z., Bragman, F., Bisdas, S., Ourselin, S., Cardoso, M.J. (2018). "Towards Safe Deep Learning: Accurately Quantifying Biomarker Uncertainty in Neural Network Predictions." pp. 1-9. In: Frangi, A., Schnabel, J., Davatzikos, C., Alberola-Lopez, C., Fichtinger, G. (eds) Medical Image Computing and Computer Assisted Intervention—MICCAI 2018. MICCAI 2018. Lecture Notes in Computer Science, vol. 11070. Springer, Cham. https://doi.org/10.1007/978-3-030-00928-1_78.
C. Cano-Espinosa, G. González, G. R. Washko, M. Cazorla and R. S. J. Estépar, "Biomarker Localization From Deep Learning Regression Networks," in IEEE Transactions on Medical Imaging, vol. 39, No. 6, pp. 2121-2132, Jun. 2020, doi: 10.1109/TMI.2020.2965486.
Kafieh R, Rabbani H, Kermani S. "A review of algorithms for segmentation of optical coherence tomography from retina." J Med Signals Sens. Jan. 2013;3(1):45-60. PMID: 24083137; PMCID: PMC3785070.
Freerk G. Venhuizen, Bram van Ginneken, Bart Liefers, Mark J.J.P. van Grinsven, Sascha Fauser, Carel Hoyng, Thomas Theelen, and Clara I. Sanchez, "Robust total retina thickness segmentation in optical coherence tomography images using convolutional neural networks," Biomed. Opt. Express 8, 3292-3316 (2017).
Hiroshi Ishikawa, Daniel M. Stein, Gadi Wollstein, Siobahn Beaton, James G. Fujimoto, Joel S. Schuman; "Macular Segmentation with Optical Coherence Tomography." Invest. Ophthalmol. Vis. Sci. 2005;46(6):2012-2017. https://doi.org/10.1167/iovs.04-0335.
Maloca PM, Lee AY, de Carvalho ER, Okada M, Fasler K, et al. (2019) "Validation of automated artificial intelligence segmentation of optical coherence tomography images." PLOS One 14(8): e0220063. pp. 1-14. https://doi.org/10.1371/journal.pone.0220063.
Zhongdi Chu, Yuxuan Cheng, Yingying Shi, Liang Wang, Xiao Zhou, Giovanni Gregori, Philip J Rosenfeld, Ruikang Wang; "A novel deep learning algorithm for hyper-transmission defects segmentation in OCT scans." Invest. Ophthalmol. Vis. Sci. 2021;62(11):44. pp. 1-4.
Zhongdi Chu, yingying shi, Xiao Zhou, Yuxuan Cheng, Rita Laiginhas, Giovanni Gregori, Philip J Rosenfeld, Ruikang K Wang; "A novel deep learning algorithm for the segmentation of pigment deposits using SS-OCT." Invest. Ophthalmol. Vis. Sci. 2021;62(8):2544. pp. 1-3.
Diaz, J. & Wang, Jay & Oellers, Patrick & Lains, Ines & Sobrin, Lucia & Husain, Deeba & Miller, Joan & Vavvas, Demetrios & Miller, John. (2018). "Imaging the Deep Choroidal Vasculature Using Spectral Domain and Swept Source Optical Coherence Tomography Angiography." Journal of VitreoRetinal Diseases. 2. 247412641877180. 10.1177/2474126418771805. pp. 1-19.
Yoon, J., Han, J., Park, J.I. et al. "Optical coherence tomography-based deep-learning model for detecting central serous chorioretinopathy." Sci Rep 10, 18852, pp. 1-9 (2020). https://doi.org/10.1038/s41598-020-75816-w.
Ran, A.R., Tham, C.C., Chan, P.P. et al. "Deep learning in glaucoma with optical coherence tomography: a review." Eye 35, 188-201 (2021). https://doi.org/10.1038/s41433-020-01191-5.
Dahrouj M, Miller JB. "Artificial Intelligence (AI) and Retinal Optical Coherence Tomography (OCT)." Semin Ophthalmol. May 19, 2021;36(4):341-345. doi: 10.1080/08820538.2021.1901123. Epub Mar. 18, 2021. PMID: 33734928.
Zhou H, Dai Y, Gregori G, Rosenfeld PR, Duncan JL, Schwartz DM, Wang RK. "Automated morphometric measurement of the retinal pigment epithelium complex and choriocapillaris using swept source OCT." Biomed Opt Express. Mar. 6, 2020;11(4):1834-1850. doi: 10.1364/BOE.385113. PMID: 32341851; PMCID: PMC7173887.
Ledesma-Gil G, Fernandez-Avellaneda P, Spaide RF. "Swept-Source Optical Coherence Tomography Angiography Imaging of the Choriocapillaris." Retina. Jul. 1, 2021;41(7):1373-1378. doi: 10.1097/IAE.0000000000003109. PMID: 33411477.
Asaoka, R. et al., "Using Deep Learning and Transfer Learning to Accurately Diagnose Early-Onset Glaucoma From Macular Optical Coherence Tomography Images," Elsevier: Deep Learning to Diagnose Glaucoma, vol. 198, 2018, pp. 136-145; https://doi.org/10.1016/j.ajo.2018.10.007.
Neveling, K. et al., "Next-Generation Genetic Testing for Retinitis Pigmentosa," Human Genome Variation Society—Human Mutation, vol. 33, No. 6, Feb. 14, 2012, pp. 963-972.
Saikia, S. et al., "Lesion detection in women breast's dynamic contrast-enhanced magnetic resonance imaging using deep learning," Scientific Reports (2023) 13:22555.
The Age-Related Eye Disease Study Research Group, "The Age-Related Eye Disease Study System for Classifying Age-related Macular Degeneration From Stereoscopic Color Fundus Photographs: The Age-Related Eye Disease Study Report Number 6," American Journal of Opthamology, vol. 132, No. 5, Elsevier: Grading Age-Related Macular Degeneration from Photographs, Nov. 2001, pp. 668-681.
Zhou, PhD, H. et al., "Age-Related Changes in Choroidal Thickness and the vol. of Vessels and Stroma Using Swept-Source OCT and Fully Automated Algorithms, " 2019, Elsevier: American Adademy of Opthamology, pp. 204-215.
International Search Report and Written Opinion mailed Aug. 26, 2022, issued in corresponding International Application No. PCT/US2022/27002, filed Apr. 29, 2022, 6 pages.

* cited by examiner

TECHNIQUES FOR AUTOMATICALLY SEGMENTING OCULAR IMAGERY AND PREDICTING PROGRESSION OF AGE-RELATED MACULAR DEGENERATION

CROSS-REFERENCE(S) TO RELATED APPLICATION

This application is a National Stage of International Application No. PCT/US2022/027002, filed Apr. 29, 2022 which claims the benefit of Provisional Application No. 63/182,328, filed Apr. 30, 2021, the entire disclosures of which are hereby incorporated by reference herein for all purposes.

BACKGROUND

Geographic atrophy (GA) is the late stage of nonexudative (dry) age-related macular degeneration (AMD), which is a major cause of vision loss worldwide. Geographic atrophy is characterized by the loss of photoreceptors, retinal pigment epithelium (RPE), and choriocapillaris (CC), and leads to irreversible vision loss where the geographic atrophy is present. Geographic atrophy is also known as complete RPE and outer retinal atrophy (cRORA). Currently there are no Food and Drug Administration approved treatments to prevent the formation or progression of geographic atrophy, but several promising therapeutic treatment clinical trials using complement inhibitors are underway.

Rather than using visual acuity as a clinical trial endpoint, most studies use the slowing of the GA enlargement rate (ER) as the clinical trial endpoint because vision is usually affected late in the disease process when the GA progresses into the foveal region. There has been a great deal of interest in identifying GA that is more likely to enlarge more rapidly, hoping not only to understand the underlying disease pathophysiology responsible for GA growth, but also to help facilitate the testing of promising therapies to slow the progression of GA against more rapidly growing GA so that clinical trials can be of shorter duration.

An automated and accurate approach to identify, segment, and quantify GA would be of great interest and importance for following patients in clinical practice and confirming the effectiveness of treatments in clinical trials, as would automated and accurate techniques for predicting GA enlargement rates.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method of automatically predicting progression of age-related macular degeneration is provided. An image analysis computing system receives optical coherence tomography data (OCT data). The image analysis computing system determines an optical attenuation coefficient for each pixel of the OCT data to create optical attenuation coefficient data (OAC data) corresponding to the OCT data. The image analysis computing system determines an area exhibiting geographic atrophy based on at least one of the OCT data and the OAC data. The image analysis computing system measures one or more attributes within an adjacent area that is adjacent to the area exhibiting geographic atrophy, and the image analysis computing system determines a predicted enlargement rate based on the one or more attributes within the adjacent area.

In some embodiments, a computer-implemented method of automatically detecting an area of an eye exhibiting geographic atrophy is provided. An image analysis computing system receives optical coherence tomography data (OCT data). The image analysis computing system determines an optical attenuation coefficient for each pixel of the OCT data to create optical attenuation coefficient data (OAC data) corresponding to the OCT data, and the image analysis computing system determines an area exhibiting geographic atrophy based on the OAC data.

In some embodiments, computer-readable media having computer-executable instructions stored thereon are provided. The instructions, in response to execution by an image analysis computing system, cause the image analysis computing system to perform one of the methods described above. In some embodiments, an image analysis computing system configured to perform one of the methods described above is provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
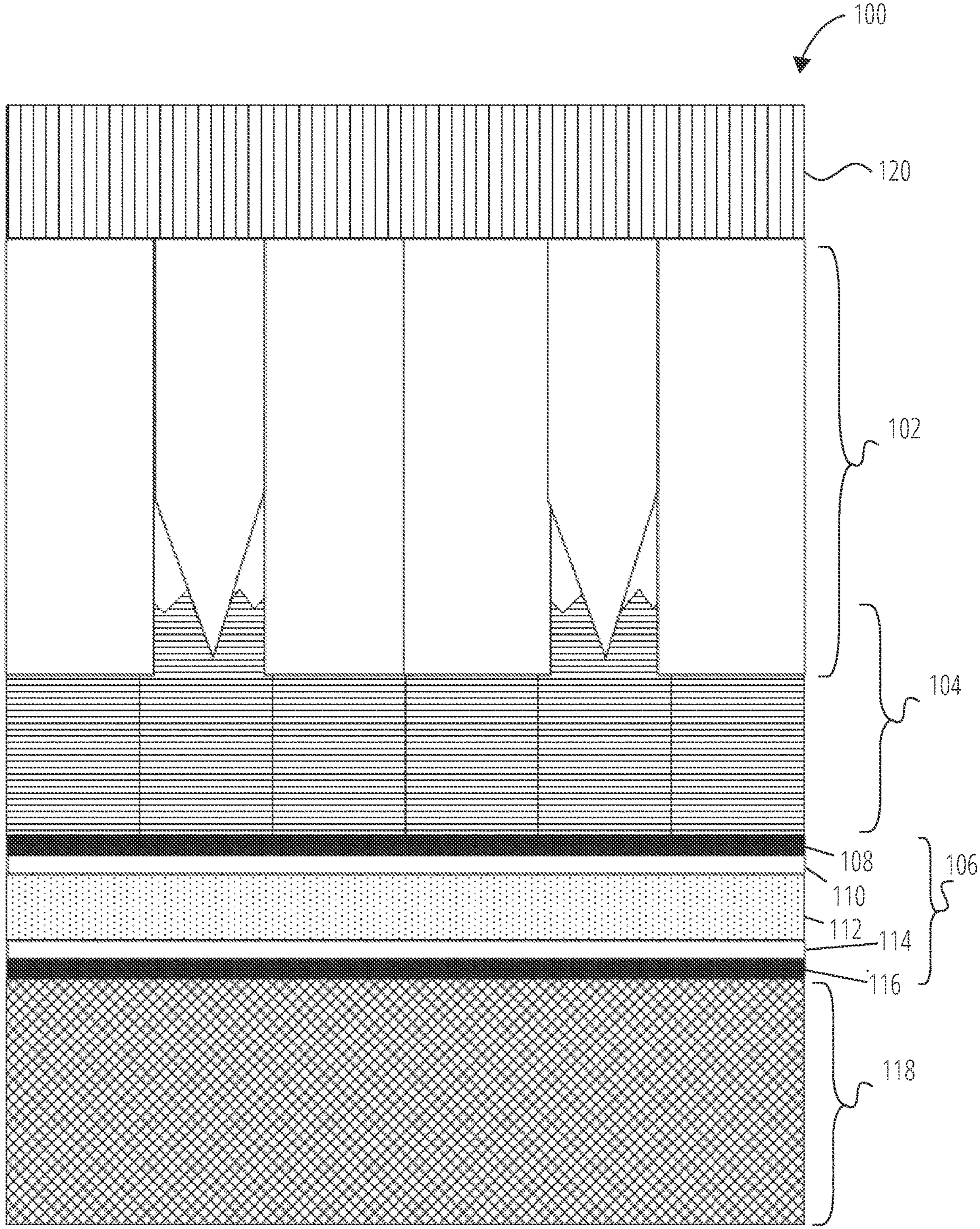
FIG. 1 is a schematic diagram of a cross-section of a rear of an eye.

Traditionally, geographic atrophy has been imaged with its enlargement rate measured using 3 major approaches: color fundus imaging (CFI), fundus autofluorescence (FAF), and optical coherence tomography (OCT). Although CFI is of historical interest, FAF and OCT imaging are currently used in clinical practice and clinical research because these imaging modalities provide better contrast for detecting the loss of the RPE, which is the sine qua non of GA.

Whereas FAF imaging provides only a 2-dimensional view of the fundus without any depth information, OCT imaging, including both spectral domain OCT (SD-OCT) and swept-source OCT (SS-OCT), are useful to visualize GA, quantify GA and measure the growth of GA. The depth-resolved nature of OCT imaging allows for layer specific visualization and the ability to differentiate the extent of anatomical changes across different layers.

In addition to using OCT B-scans, en face OCT imaging is a useful strategy for visualizing GA, and the use of boundary-specific segmentation by using a choroidal slab under the RPE allows for an en face image that specifically accentuates the choroidal hypertransmission defects (hyper-TDs) that arise when the RPE is absent.

In the present disclosure, a novel deep learning approach is provided to identify and segment GA areas using optical attenuation coefficients (OACs) calculated from OCT data. Novel en face OAC images are used to identify and visualize GA, and machine learning models are used for the task of automatic GA identification and segmentation. In some embodiments, once GA areas are segmented, measurements in an adjacent area to the GA are obtained of at least one of an RPE-BM distance, an outer retinal thickness, and a choriocapillaris flow deficit, and a predicted enlargement rate of the GA is determined based on the measurements.

According to Classification of Atrophy Meetings (CAM) consensus, the definition of geographic atrophy or complete retinal pigment epithelial and outer retinal atrophy (cRORA) is defined by 3 inclusive OCT criteria: (1) region of hyperTD with at least 250 μm in its greatest linear dimension, (2) zone of attenuation or disruption of the RPE of at least 250 μm in its greatest linear dimension, and (3) evidence of overlying photoreceptor degeneration; and 1 exclusive criteria: the presence of scrolled RPE or other signs of an RPE tear. This definition of geographic atrophy or cRORA relies solely on average B-scans, but en face imaging of geographic atrophy using the subRPE slab is a convenient alternative for the detection of geographic atrophy using fundus autofluorescence and conventional OCT B-scans. The proposed approaches described herein using OAC data are particularly suitable for geographic atrophy identification because they allow en face views with direct three-dimensional information of RPE attenuation and disruption. OAC quantifies the tissues' ability to attenuate (absorb and scatter) light, meaning that it is particularly useful to identify high pigmentation (or the lack of) in retinal tissues.

Using a custom slab and en face imaging strategy with OAC data, the RPE may be visualized with strong contrast. When RPE cells die and lose pigments, their OAC values are reduced as well, resulting in a dark appearance on the false color images described below. In addition to the enhanced contrast for attenuated or disrupted RPE, the OAC approach described herein also provides similar depth-resolved advantages available in traditional OCT approaches. By incorporating three different en face images from the same slab in the false color images based on the OAC data, depth-resolved information—namely the RPE elevation information—is provided on an en faceview. This approach is also useful for identifying drusen or other forms of RPE elevation in AMD eyes.

FIG. 1 is a schematic diagram of a cross-section of a rear of an eye. The anatomy of this area, as well as the rest of the eye, is well-known to those of ordinary skill in the art, but the diagram 100 and its description is provided in order to provide context to the remainder of the disclosure. In the diagram 100, the labeled layers proceed from an innermost labeled layer to an outermost labeled layer while proceeding downward through the diagram.

The illustration shows a layer of rods and cones 102 (photoreceptors), a retinal pigment epithelium 104 (also referred to as the RPE), a Bruch's membrane 106 (also referred to as the BM), and a choriocapillaris 118. The Bruch's membrane 106 includes an RPE basement membrane 108, an inner collagenous zone 110, a region of central elastic fiber bands 112, an outer collagenous zone 114, and a choroid basement membrane 116. Those of ordinary skill in the art will understand the location and biological function of the labeled structures of the diagram 100, as well as the anatomy of portions of the eye that are not illustrated.

Figure 2:
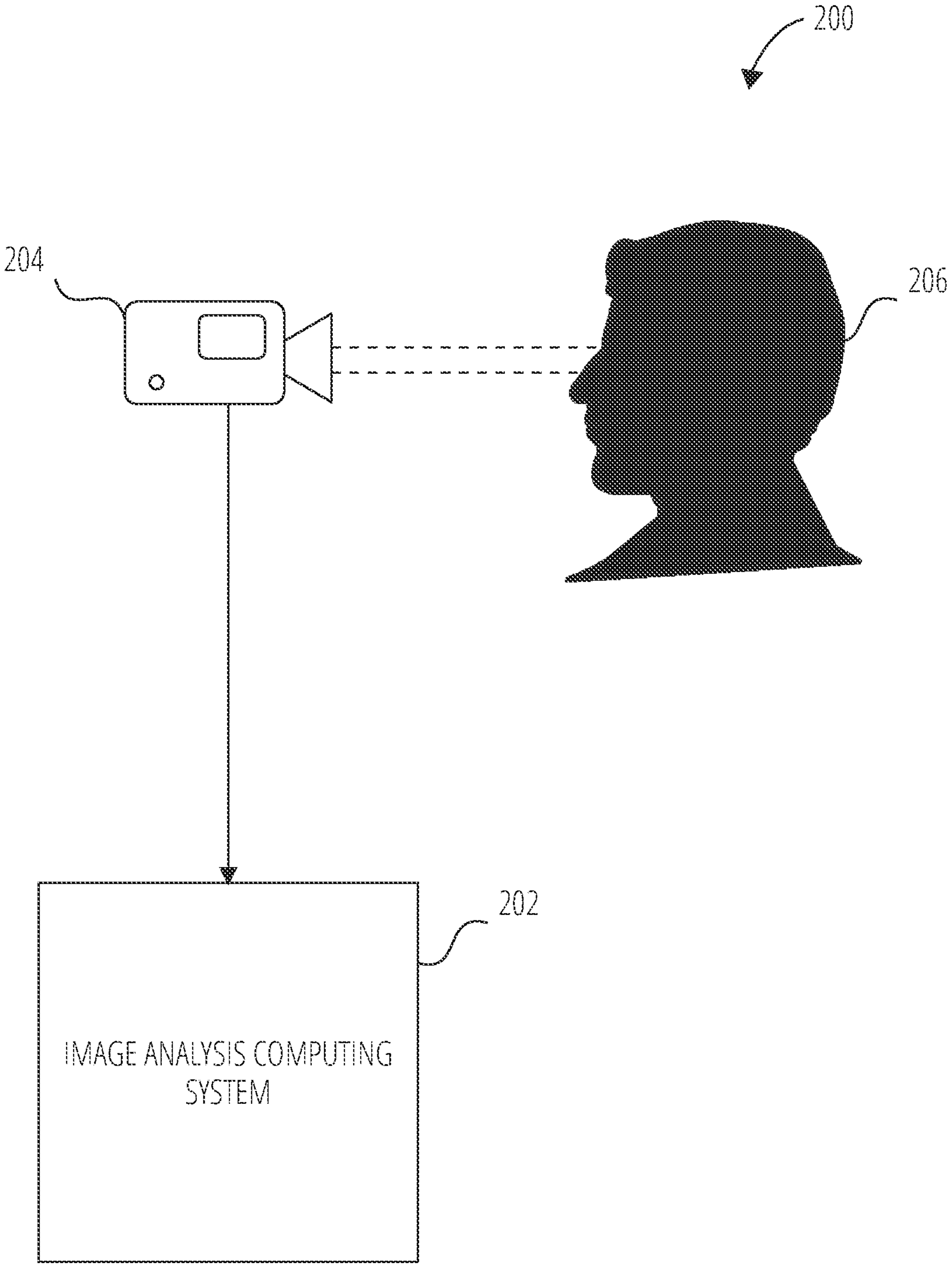
FIG. 2 is a schematic illustration of a system configured to obtain ocular imagery, to automatically segment and measure the imagery, and to predict progression of age-related macular degeneration according to various aspects of the present disclosure.

FIG. 2 is a schematic illustration of a system configured to obtain ocular imagery, to automatically segment and measure the imagery, and to predict progression of age-related macular degeneration according to various aspects of the present disclosure.

As shown, the system 200 includes an image analysis computing system 202 and an optical coherence tomagraphy (OCT) imaging system 204. The OCT imaging system 204 is configured to obtain OCT data representing an eye of a subject 206, and to provide the OCT data to the image analysis computing system 202 for segmentation, measurement, and prediction.

In some embodiments, the OCT imaging system 204 is configured to use light waves to generate both en face imagery (also referred to as A-lines) at one or more depths and cross-sectional imagery (also referred to as B-lines) at one or more locations. In some embodiments, the OCT imaging system 204 may use swept-source OCT (SS-OCT) technology. In some embodiments, the OCT imaging system 204 may use spectral-domain OCT (SD-OCT) technology. In some embodiments, other forms of OCT technology may be used. One non-limiting example of an OCT imaging system 204 suitable for use with the present disclosure is the PLEX® Elite 9000, manufactured by Carl Zeiss Meditec of Dublin, CA. This instrument uses a 100 kHz light source with a 1050 nm central wavelength and a 100 nm bandwidth, resulting in an axial resolution of about 5.5 μm and a lateral resolution of about 20 μm estimated at the retinal surface.

Such an instrument may be used to create 6×6 mm scans, for which there are 1536 pixels on each A-line (3 mm), 600 A-lines on each B-scan, and 500 sets of twice-repeated B-scans.

In some embodiments, the OCT imaging system 204 is communicatively coupled to the image analysis computing system 202 using any suitable communication technology, including but not limited to wired technologies (e.g., Ethernet, USB, FireWire, etc.), wireless technologies (e.g., WiFi, WiMAX, 3G, 4G, LTE, Bluetooth, etc.), exchange of removable computer-readable media (e.g., flash memory, optical disks, magnetic disks, etc.), and combinations thereof. In some embodiments, the OCT imaging system 204 performs some processing of the OCT data before providing the OCT data to the image analysis computing system 202 and/or upon request by the image analysis computing system 202.

Figure 3:
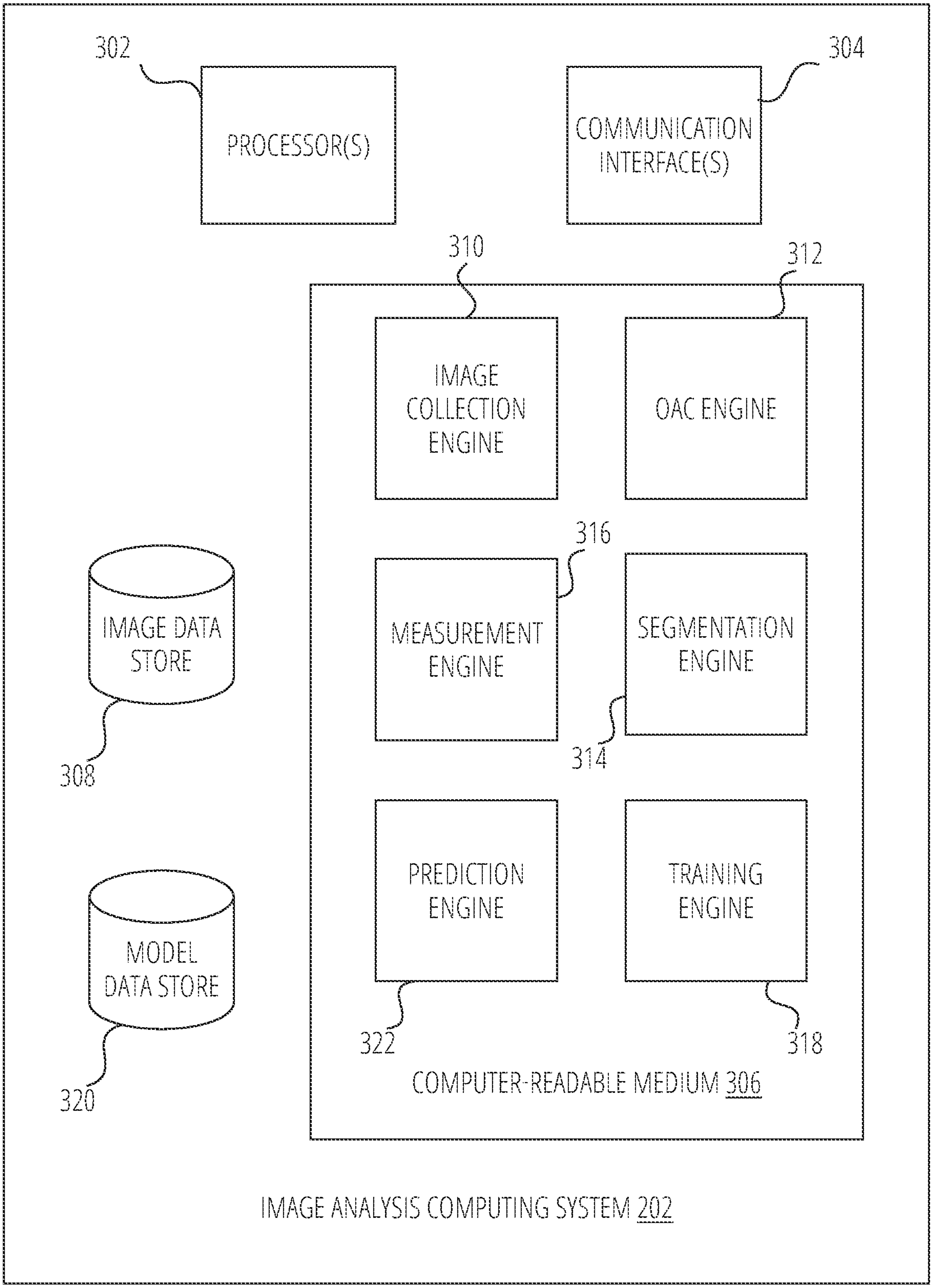
FIG. 3 is a block diagram that illustrates aspects of a non-limiting example embodiment of an image analysis computing system according to various aspects of the present disclosure.

FIG. 3 is a block diagram that illustrates aspects of a non-limiting example embodiment of an image analysis computing system according to various aspects of the present disclosure. The illustrated image analysis computing system 202 may be implemented by any computing device or collection of computing devices, including but not limited to a desktop computing device, a laptop computing device, a mobile computing device, a server computing device, a computing device of a cloud computing system, and/or combinations thereof. The image analysis computing system 202 is configured to receive OCT data from the OCT imaging system 204, automatically segment the OCT data to detect areas of geographic atrophy, measure attributes of one or more adjacent areas adjacent to the areas of geographic atrophy, and use the attributes to predict progression of the geographic atrophy.

As shown, the image analysis computing system 202 includes one or more processors 302, one or more communication interfaces 304, an image data store 308, a model data store 320, and a computer-readable medium 306.

In some embodiments, the processors 302 may include any suitable type of general-purpose computer processor. In some embodiments, the processors 302 may include one or more special-purpose computer processors or AI accelerators optimized for specific computing tasks, including but not limited to graphical processing units (GPUs), vision processing units (VPTs), and tensor processing units (TPUs).

In some embodiments, the communication interfaces 304 include one or more hardware and or software interfaces suitable for providing communication links between components. The communication interfaces 304 may support one or more wired communication technologies (including but not limited to Ethernet, FireWire, and USB), one or more wireless communication technologies (including but not limited to Wi-Fi, WiMAX, Bluetooth, 2G, 3G, 4G, 5G, and LTE), and/or combinations thereof.

As shown, the computer-readable medium 306 has stored thereon logic that, in response to execution by the one or more processors 302, cause the image analysis computing system 202 to provide an image collection engine 310, an OAC engine 312, a segmentation engine 314, a measurement engine 316, a training engine 318, and a prediction engine 322.

As used herein, "computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

In some embodiments, the image collection engine 310 is configured to receive OCT data from the OCT imaging system 204. In some embodiments, the image collection engine 310 may also be configured to collect training images from one or more storage locations, and to store the training images in the image data store 308. In some embodiments, the OAC engine 312 is configured to calculate OAC data based on OCT data received from the OCT imaging system 204.

In some embodiments, the training engine 318 is configured to train one or more machine learning models to label areas of geographic atrophy depicted in at least one of OAC data and OCT data. In some embodiments, the segmentation engine 314 is configured to use suitable techniques to label areas of geographic atrophy in images collected by the image collection engine 310 and/or OAC data generated by the OAC engine 312. In some embodiments, the techniques may include using machine learning models from the model data store 320 to automatically label images. In some embodiments, the techniques may include receiving labels manually entered by expert reviewers.

In some embodiments, the measurement engine 316 is configured to measure one or more attributes of an eye depicted in OAC data. In some embodiments, the prediction engine 322 is configured to predict an enlargement rate of geographic atrophy for an eye based on the attributes measured by the measurement engine 316.

Further description of the configuration of each of these components is provided below.

As used herein, "engine" refers to logic embodied in hardware or software instructions, which can be written in one or more programming languages, including but not limited to C, C++, C#, COBOL, JAVA™, PHP, Perl, HTML, CSS, Javascript, VBScript, ASPX, Go, and Python. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 4:
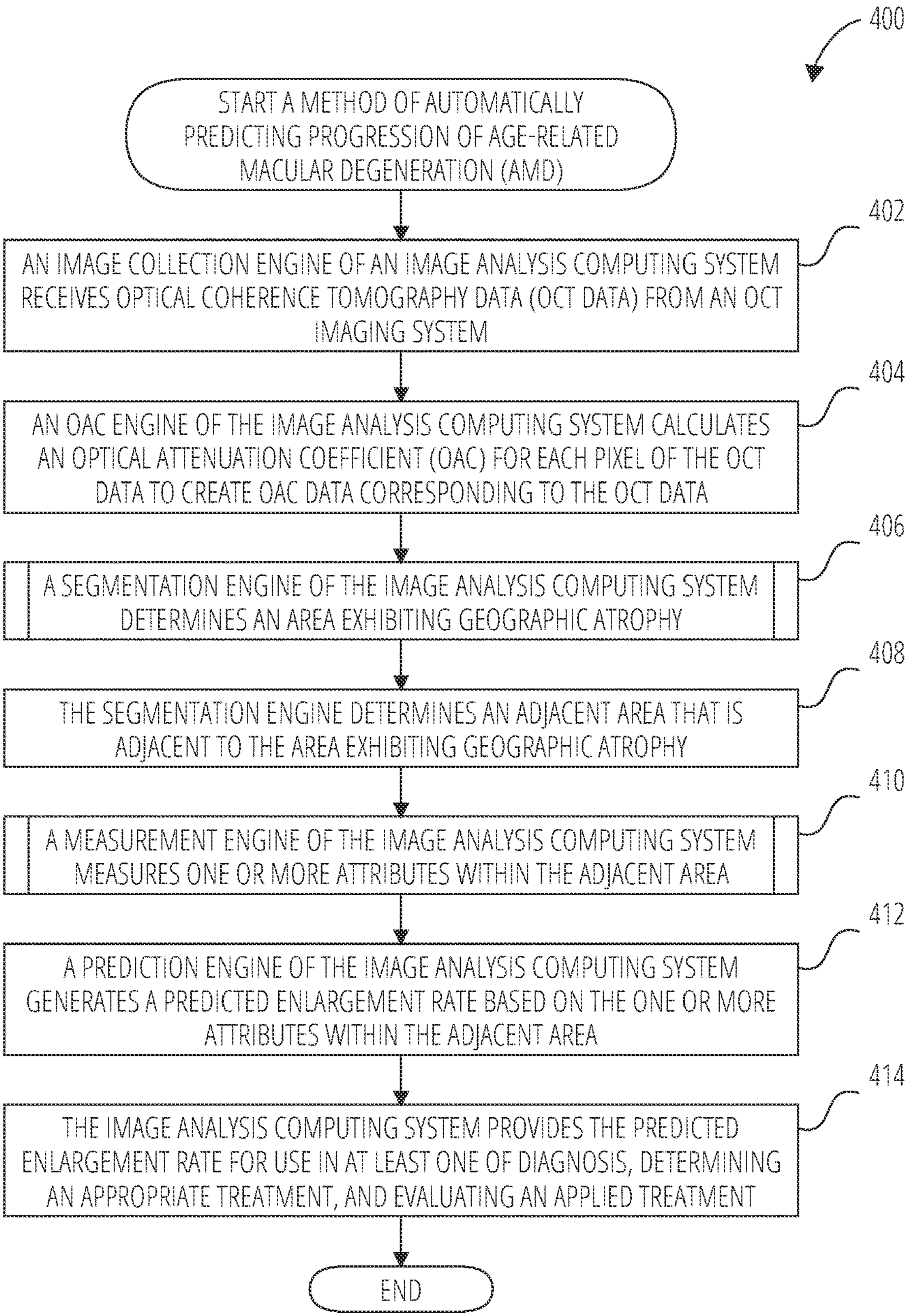
FIG. 4 is a flowchart that illustrates a non-limiting example embodiment of a method of automatically predicting progression of age-related macular degeneration (AMD) according to various aspects of the present disclosure.

FIG. 4 is a flowchart that illustrates a non-limiting example embodiment of a method of automatically predicting progression of age-related macular degeneration (AMD) according to various aspects of the present disclosure. In the method 400, an image analysis computing system 202 is used to automatically segment OCT data representing an eye to identify areas of geographic atrophy, and automatically measure attributes of adjacent areas adjacent to the areas of geographic atrophy. The measured attributes may then be used to predict a progression of the geographic atrophy in the eye, and the predicted progression may be used as a diagnosis of AMD, for determining an appropriate treatment, for evaluating an applied treatment, or for any other suitable purpose. The techniques described in the method 400 provide technical improvements, at least by improving the quality of the segmentation of the geographic atrophy and by enabling automatic prediction and improving the quality of the prediction of progression of geographic atrophy.

From a start block, the method 400 advances to block 402, where an image collection engine 310 of an image analysis computing system 202 receives optical coherence tomography data (OCT data) from an OCT imaging system 204. It will be understood that, given the presence of A-lines and B-scans, the OCT data constitutes a volumetric image of the scanned area. The OCT data may be SS-OCT data, SD-OCT data, or any other suitable form of OCT data. In some embodiments, the OCT data includes both A-lines and B-scans. In some embodiments, the OCT data may include 6×6 mm scans with 1536 pixels on each A-line (3 mm), 600 A-lines on each B-scan, and 600 sets of twice repeated B-scans. In some embodiments, scans with a signal strength less than a signal strength threshold (such as 7) or evident motion artifacts may be excluded.

At block 404, an OAC engine 312 of the image analysis computing system 202 calculates an optical attenuation coefficient (OAC) for each pixel of the OCT data to create OAC data corresponding to the OCT data. In some embodiments, the OAC may be calculated for each pixel using a depth-resolved single scattering model. Briefly, if it is assumed that all light is completely attenuated within the imaging range, the backscattered light is a fixed fraction of the attenuated light, and the detected light intensity is uniform over a pixel, then the OAC μ[i] at each pixel i within the volumetric imaging range may be determined by:

$$\mu[i] = \frac{I[i]}{2\Delta \int_{i+1}^{\infty} I[i]}$$

wherein Δ is an axial size of each pixel, I[i] is a detected OCT signal intensity at the ith pixel; and $$\int_{i+1}^{\infty} I[i]$$

is calculated by adding OCT signal intensities of all pixels beneath the ith pixel; and ith pixel. Because all light is assumed to be fully attenuated within the imaging range, $$\int_{i+1}^{\infty} I[i]$$

can be calculated by adding up the OCT intensities of all pixels beneath the range, ith pixel. In some embodiments, log-scale OCT data may be converted back to a linear scale before calculating the OAC data. In some embodiments, this conversion may be performed by the OCT imaging system 204, or by the image analysis computing system 202 using an engine provided by a manufacturer of the OCT imaging system 204.

Figure 6:
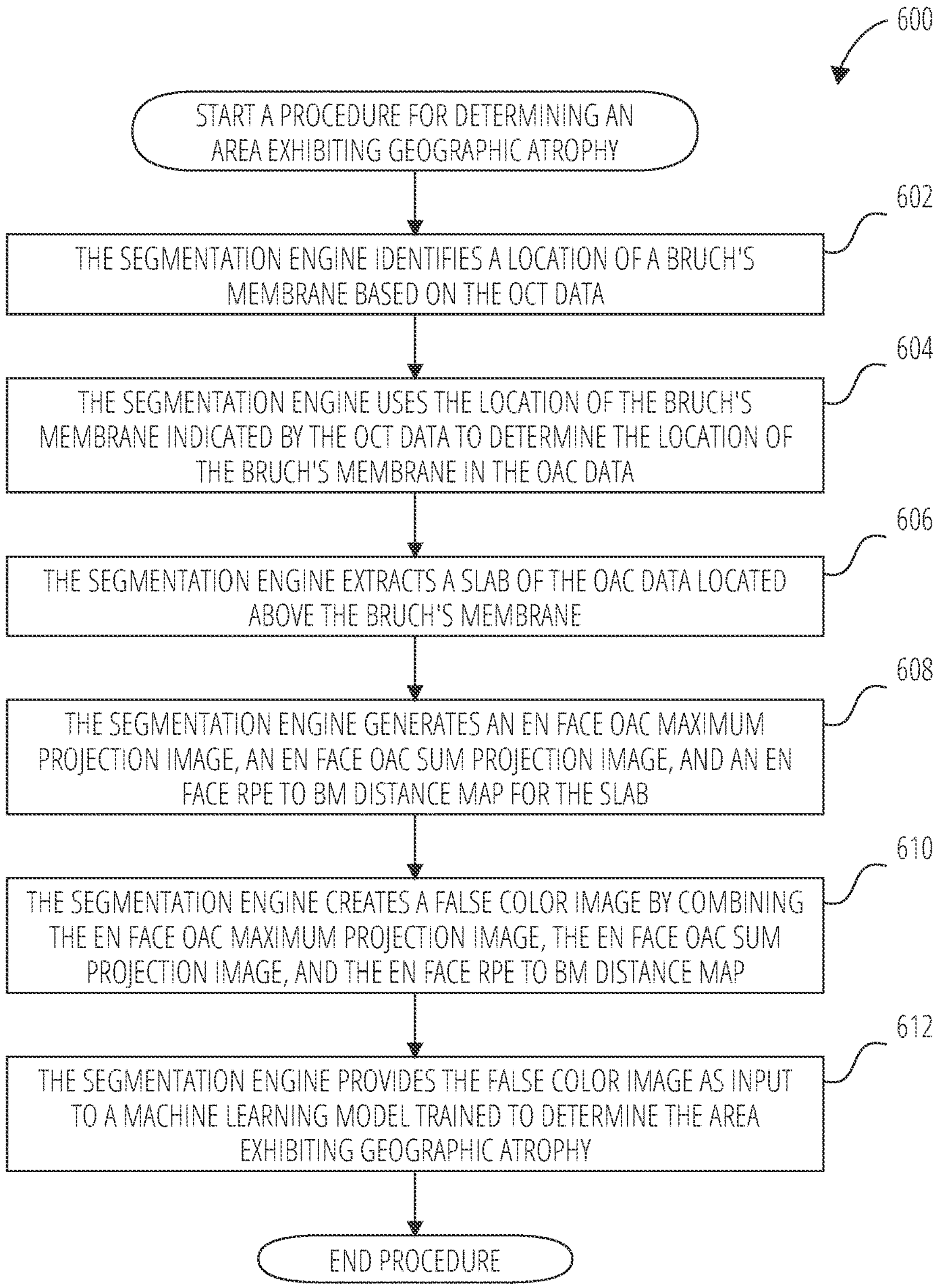
FIG. 6 is a flowchart that illustrates a non-limiting example embodiment of a procedure for determining an area exhibiting geographic atrophy according to various aspects of the present disclosure.

At subroutine block 406, a segmentation engine 314 of the image analysis computing system 202 determines an area exhibiting geographic atrophy. Any suitable technique for determining the area exhibiting geographic atrophy may be used. In some embodiments, an automatic technique for determining the area exhibiting geographic atrophy may be used. One non-limiting example of a technique that uses the OAC data to automatically detect areas exhibiting geographic atrophy using a machine learning model is illustrated in FIG. 6 and discussed in further detail below. Another non-limiting example of a different automatic technique is to provide en face images generated from the OCT data to a machine learning model similar to that discussed in FIG. 6, though the use of the OAC data has been found to provide more accurate results.

In some embodiments, a manual technique for determining the area exhibiting geographic atrophy may be used, with the subsequent measurement and prediction steps being performed automatically. If using a manual technique, the segmentation engine 314 may cause images representing the OCT data and/or the OAC data to be presented to a clinician, and the clinician may manually indicate areas exhibiting geographic atrophy via a user interface provided by the segmentation engine 314.

At block 408, the segmentation engine 314 determines an adjacent area that is adjacent to the area exhibiting geographic atrophy. The segmentation engine 314 determines the adjacent area by finding an area that is within a specified area adjacent to the area exhibiting geographic atrophy. Any suitable adjacent area may be used. As one non-limiting example, the adjacent area may be a 1-degree rim region that extends from 0 μm outside of the margin of the area exhibiting geographic atrophy to 300 μm outside of the margin of the area exhibiting geographic atrophy. As another non-limiting example, the adjacent area may be an additional 1-degree rim region that extends from 300 μm outside of the margin of the area exhibiting geographic atrophy to 600 μm outside of the margin of the area exhibiting geographic atrophy. As yet another non-limiting example, the adjacent area may be a 2-degree rim region that extends from 0 μm outside of the margin of the area exhibiting geographic atrophy to 600 μm outside of the margin of the area exhibiting geographic atrophy. As still another non-limiting example, the adjacent area may be an area from 600 μm outside of the margin of the area exhibiting geographic atrophy to the edge of the scan area. As a final non-limiting example, the adjacent area may be an entire area from the margin of the area exhibiting geographic atrophy to the edge of the scan area. In some embodiments, the listed sizes of these areas may be approximate, and may be smaller or larger by 5% (e.g., a region that extends from 0 μm outside of the margin of the area exhibiting geographic atrophy to an amount between 285 μm to 315 μm outside of the margin of the area exhibiting geographic atrophy, etc.).

Figure 5:
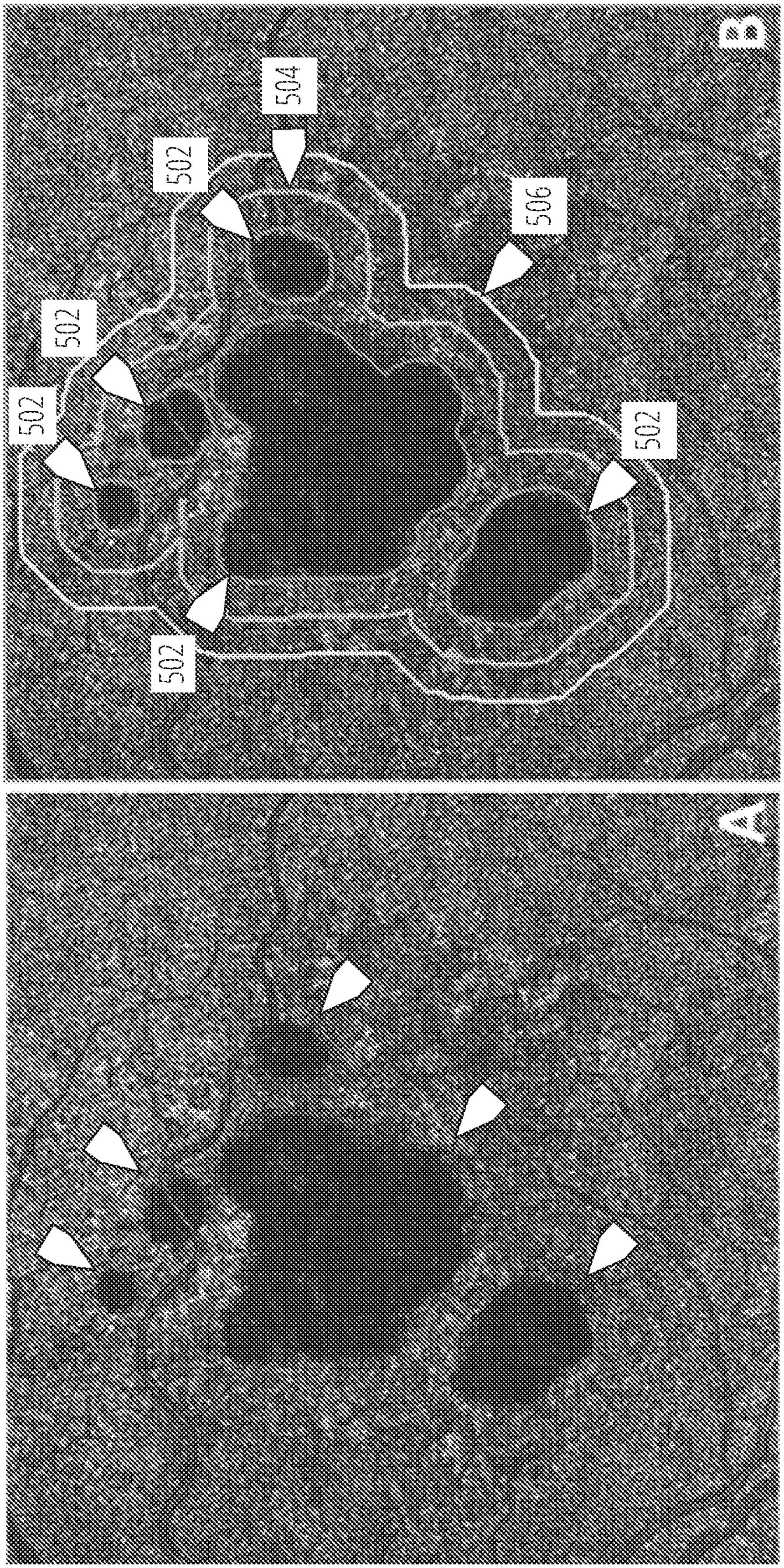
FIG. 5 provides example imagery in order to illustrate the described adjacent areas of the present disclosure.

FIG. 5 provides example imagery in order to illustrate the described adjacent areas of the present disclosure. In FIG. 5, Image A is an en faceOAC maximum projection image, with areas of geographic atrophy marked with white arrowheads. Image B provides the same image with boundaries of various adjacent areas. Boundaries of geographic atrophy 502 are established and indicated with a first set of lines. A 1-degree rim region adjacent area is defined between the boundaries of geographic atrophy 502 and a 1-degree rim region border 504. An additional 1-degree rim region adjacent area is defined between the 1-degree rim region border 504 and a 2-degree rim region border 506. A 2-degree rim region adjacent area is defined between the boundaries of geographic atrophy 502 and the 2-degree rim region border 506. Another adjacent area (the R3 area) is defined between the 2-degree rim region border 506 and the edge of the image, and a final adjacent area (the total scan area minus GA) is defined between the boundaries of geographic atrophy 502 and the edge of the image.

Returning to FIG. 4, at subroutine block 410, a measurement engine 316 of the image analysis computing system 202 measures one or more attributes within the adjacent area. Any attributes suitable for evaluating and predicting the progression of geographic atrophy may be measured within the adjacent area. In some embodiments, the measurement engine 316 automatically measures a distance between the retinal pigment epithelium 104 and the Bruch's membrane 106 within the adjacent area (see the illustrated procedure in FIG. 7A for a non-limiting example). In some embodiments, the measurement engine 316 automatically measures an outer retinal thickness within the adjacent area (see the illustrated procedure in FIG. 7B for a non-limiting example). In some embodiments, the measurement engine 316 automatically measures a choriocapillaris flow deficit within the adjacent area (see the illustrated procedure in FIG. 7C (deleted) for a non-limiting example).

In some embodiments, the one or more attributes may include one or more features based on the measurements, including but not limited to one or more of a mean of the measurements within the adjacent area and a standard deviation of the measurements within the adjacent area. In some embodiments, different attributes may be measured within different adjacent areas (for example, a first attribute may be measured in a first adjacent area, while a second attribute is measured in a second adjacent area).

At block 412, a prediction engine 322 of the image analysis computing system 202 generates a predicted enlargement rate based on the one or more attributes within the adjacent area. In some embodiments, the prediction engine 322 retrieves a prediction model from the model data store 320 that corresponds to the adjacent area and the one or more measured attributes, and uses the prediction model to generate the predicted enlargement rate. In some embodiments, the prediction model may be a multiple linear regression model that uses one or more attributes measured in one or more adjacent areas as input, and that outputs a predicted enlargement rate. Two non-limiting examples of prediction models are described below in Example One and Example Two.

At block 414, the image analysis computing system 202 provides the predicted enlargement rate for use in at least one of diagnosis, determining an appropriate treatment, and evaluating an applied treatment. By being able to automatically predict an enlargement rate using the prediction model, a subject can be advised about the severity of their AMD and the urgency of treatment without needing to wait to observe the actual progression of the condition. Further, the efficacy of applied treatments can be evaluated without having to wait to observe the effects over long periods of time, and can instead be evaluated during or shortly after the course of treatment, thus improving the efficacy of the treatment.

The method 400 then proceeds to an end block and terminates.

FIG. 6 is a flowchart that illustrates a non-limiting example embodiment of a procedure for determining an area exhibiting geographic atrophy according to various aspects of the present disclosure. In the procedure 600, the OCT data is analyzed to generate OAC data, and the OAC data is analyzed and provided to a machine learning model in order to determine the areas exhibiting geographic atrophy.

From a start block, the procedure 600 advances to block 602, where the segmentation engine 314 identifies a location of a Bruch's membrane 106 based on the OCT data. In some embodiments, a manufacturer of the OCT imaging system 204 may provide an engine for identifying the location of the Bruch's membrane 106, and the engine may be executed by the OCT imaging system 204 or the segmentation engine 314. In some embodiments, the manufacturer of the OCT imaging system 204 may provide logic for identifying the location of the Bruch's membrane 106, and the logic may be incorporated into the segmentation engine 314. One non-limiting example of such an engine is provided by Carl Zeiss Meditec, of Dublin, CA. In some embodiments, similar techniques may be used to identify the locations of other structures within the OCT data, including but not limited to a lower boundary of a retinal nerve fiber layer (RNFL).

At block 604, the segmentation engine 314 uses the location of the Bruch's membrane 106 indicated by the OCT data to determine the location of the Bruch's membrane 106 in the OAC data. Since the OAC data is derived from the OCT data as described at block 404, the location of each volumetric pixel in the OAC data corresponds to a location of a volumetric pixel in the OCT data. Accordingly, the determined location of the Bruch's membrane 106 (and/or other detected structures) from the OCT data may be transferred to the corresponding locations in the OAC data.

At block 606, the segmentation engine 314 extracts a slab of the OAC data located above the Bruch's membrane 106. In some embodiments, the extracted slab of the OAC data may extend from the Bruch's membrane 106 to the RNFL. In some embodiments, the extracted slab of the OAC data may be a predetermined thickness, such as extending from the Bruch's membrane 106 to a predetermined distance above the Bruch's membrane 106. In one non-limiting example embodiment, the predetermined distance may be a value within a range of 540 μm to 660 μm, such as 600 μm.

At block 608, the segmentation engine 314 generates an en face OAC maximum projection image, an en face OAC sum projection image, and an en face RPE to BM distance map for the slab. The en face OAC maximum projection image represents maximum OAC values through the depth of the slab for each given pixel. The en face OAC sum projection image represents a sum of the OAC values through the depth of the slab for each given pixel. The en face RPE-BM distance map represents a measured distance between the retinal pigment epithelium 104 and the Bruch's membrane 106 at each pixel. In some embodiments, the location of the retinal pigment epithelium 104 may be determined by the pixel with the maximum OAC value above the Bruch's membrane 106 along each A-line.

At block 610, the segmentation engine 314 creates a false color image by combining the en face OAC maximum projection image, the en face OAC sum projection image, and the en face RPE to BM distance map. Each image may be assigned to a color channel for the false color image in order to combine the separate images. For example, the value for a pixel for the en face OAC maximum projection image may be assigned to the red channel, the value for a corresponding pixel from the en face OAC sum projection image may be assigned to the green channel, and the value for a corresponding pixel from the en face RPE to BM distance map may be assigned to the blue channel.

In some embodiments, the values of the separate images may be assigned to specific dynamic ranges in order to normalize the values for the false color image. As one non-limiting example, the values in the en face OAC maximum projection image may be assigned to a dynamic range of 0 to 60 $mm^{-1}$, the values in the en face OAC sum projection image may be assigned to a dynamic range of 0 to 600 (unitless), and the values in the en face RPE to BM distance map may be assigned to a dynamic range of 0 to 100 μm. In some embodiments, different dynamic ranges may be used, including dynamic ranges of other units and dynamic ranges with upper bounds that vary by up to 10% from the listed values above. In some embodiments, a smoothing filter may be applied to the false color image to reduce noise. One example of a suitable smoothing filter to be used is a 5×5 pixel median filter, though in other embodiments, other smoothing filters may be used.

Figure 8:
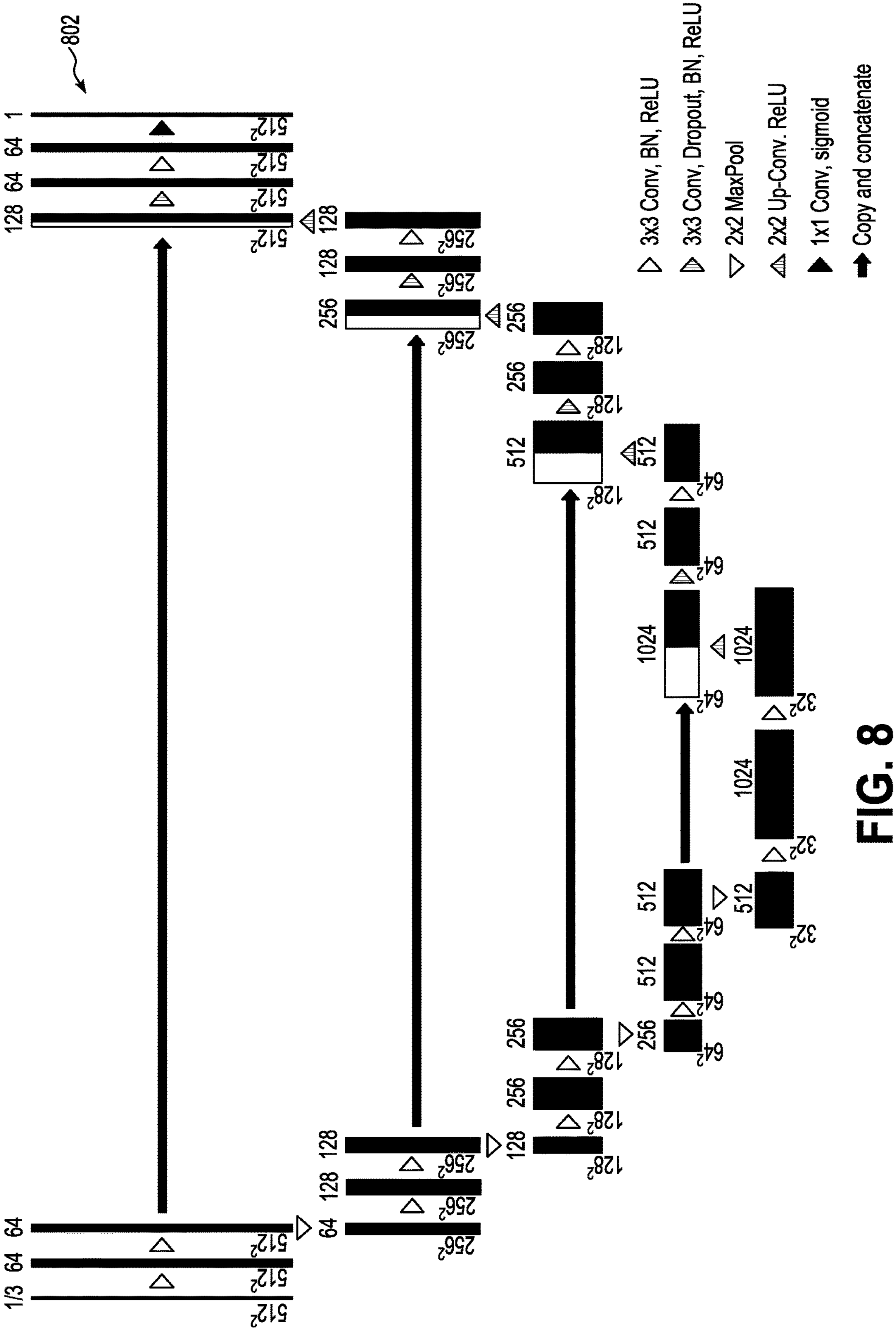
FIG. 8 is a non-limiting example embodiment of a machine learning model for performing a geographic atrophy segmentation task according to various aspects of the present disclosure.

At block 612, the segmentation engine 314 provides the false color image as input to a machine learning model trained to determine the area exhibiting geographic atrophy. In some embodiments, the false color image may be resized to match a dimension of an input layer of the machine learning model. Any suitable machine learning model may be used that accomplishes the segmentation task of the false color image (that is, that provides an identification of whether or not each pixel represents a location of geographic atrophy), including but not limited to an artificial neural network. One non-limiting example of a suitable machine learning model is a U-net, and a non-limiting example of an architecture of a suitable U-net and techniques for training are illustrated in FIG. 8 and described in detail below.

The procedure 600 then proceeds to an end block, where the segmentation that constitutes an indication of areas that exhibit geographic atrophy in the OAC data is returned to the procedure's caller, and the procedure 600 terminates.

Figure 7A:
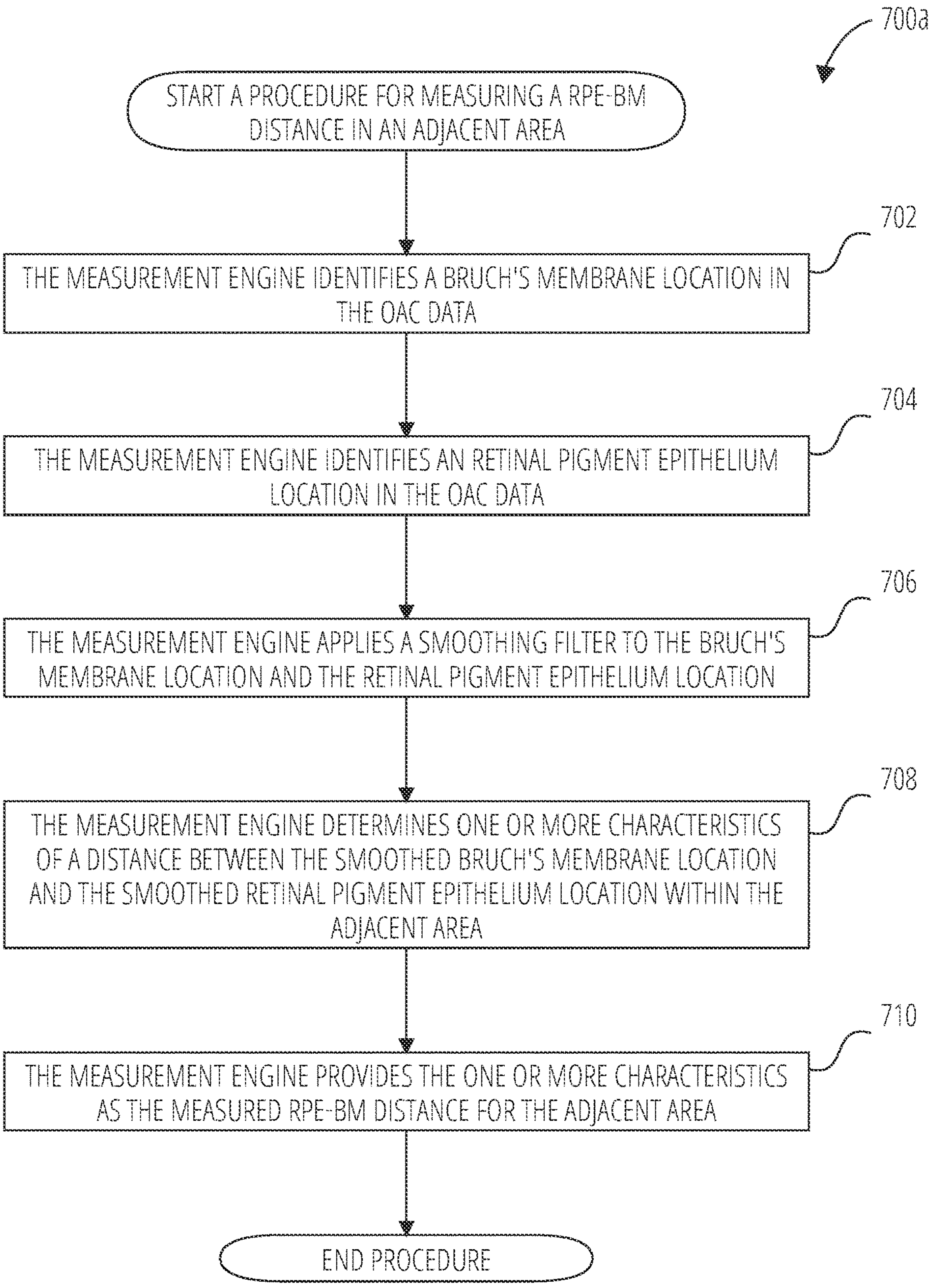
FIG. 7A is a non-limiting example embodiment of a procedure for measuring an RPE-BM distance in an adjacent area according to various aspects of the present disclosure.

FIG. 7A is a non-limiting example embodiment of a procedure for measuring an RPE-BM distance in an adjacent area according to various aspects of the present disclosure. The RPE-BM distance is an example of an attribute that may be useful in generating predicted enlargement rates. The RPE-BM distance may also be used to generate an en face RPE to BM distance map to provide as input to a machine learning model for automatic segmentation of areas of geographic atrophy.

From a start block, the procedure 700*a* advances to block 702, where the measurement engine 316 identifies a Bruch's membrane 106 location in the OAC data. In some embodiments, techniques similar to those described in block 602 may be used to identify the Bruch's membrane 106 location. In some embodiments, the Bruch's membrane 106 location previously determined at block 602 may be reused by block 702.

At block 704, the measurement engine 316 identifies a retinal pigment epithelium 104 location in the OAC data. In some embodiments, the retinal pigment epithelium 104 location may be identified by the pixel with the maximum OAC value above the Bruch's membrane 106 location along each A-line.

At block 706, the measurement engine 316 applies a smoothing filter to the Bruch's membrane 106 location and the retinal pigment epithelium 104 location. In some embodiments, a 5×5 pixel median filter may be used for the smoothing.

At block 708, the measurement engine 316 determines one or more characteristics of a distance between the smoothed Bruch's membrane 106 location and the smoothed retinal pigment epithelium 104 location within the adjacent area. Any suitable characteristics of the distance may be used. In some embodiments, a mean of the distance within the adjacent area may be used. In some embodiments, a standard deviation of the distance within the adjacent area may be used. In some embodiments, other statistical characteristics of the distance within the adjacent area may be used as attributes.

At block 710, the measurement engine 316 provides the one or more characteristics as the measured RPE-BM distance attribute for the adjacent area. The procedure 700*a* then advances to an end block and terminates.

Figure 7B:
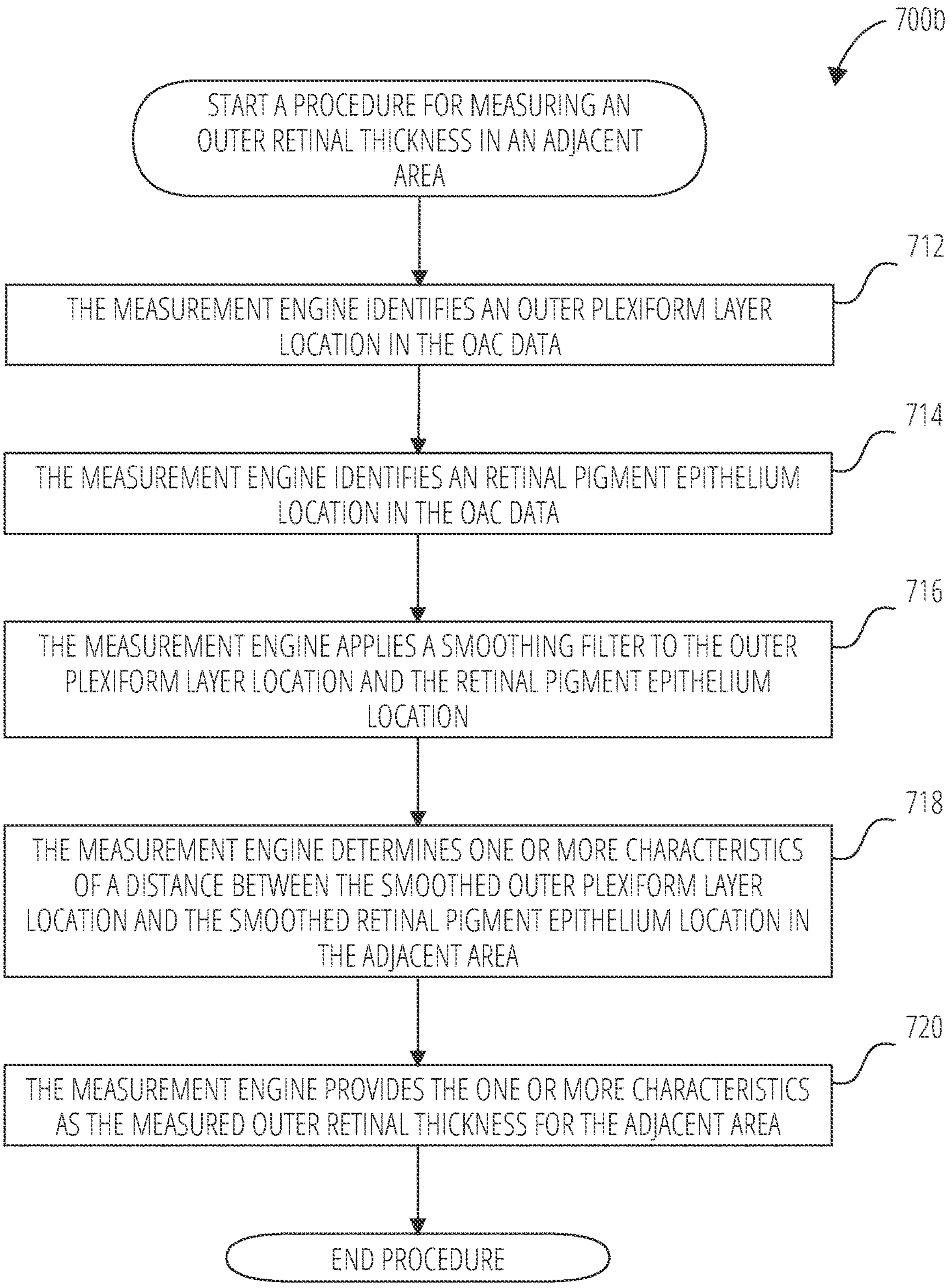
FIG. 7B is a non-limiting example embodiment of a procedure for measuring an outer retinal thickness in an adjacent area according to various aspects of the present disclosure.

FIG. 7B is a non-limiting example embodiment of a procedure for measuring an outer retinal thickness in an adjacent area according to various aspects of the present disclosure. The outer retinal thickness is another example of an attribute that may be useful in generating predicted enlargement rates. In some embodiments, the outer retinal thickness may defined as the distance from the upper boundary of the outer plexiform layer 120 to the retinal pigment epithelium 104.

From a start block, the procedure 700*b* advances to block 712, where the measurement engine 316 identifies an outer plexiform layer 120 location in the OAC data. In some embodiments, the upper boundary of the outer plexiform layer 120 may be detected using a known semi-automated segmentation technique, such as the technique described in Yin X, Chao J R, Wang R K; User-guided segmentation for volumetric retinal optical coherence tomography images; *J Biomed Opt.* 2014; 19(8):086020; doi:10.1117/1.JBO.19.8.086020, the entire disclosure of which is hereby incorporated by reference herein for all purposes.

At block 714, the measurement engine 316 identifies a retinal pigment epithelium 104 location in the OAC data. As discussed above with respect to block 704, the retinal pigment epithelium 104 location may be identified by the pixel with the maximum OAC value above the Bruch's membrane 106 location along each A-line.

At block 716, the measurement engine 316 applies a smoothing filter to the outer plexiform layer 120 location and the retinal pigment epithelium 104 location. As discussed above, the smoothing filter may be a 5×5 pixel median filter, which may be applied to the B-scan of the OAC data.

At block 718, the measurement engine 316 determines one or more characteristics of a distance between the smoothed outer plexiform layer 120 location and the smoothed retinal pigment epithelium 104 location in the adjacent area. As with the characteristics of the RPE-BM distance, any suitable characteristics of the distance between the smoothed outer plexiform layer 120 location and the smoothed retinal pigment epithelium 104 location may be used as the characteristics, including but not limited to a mean, a standard deviation, or combinations thereof.

At block 720, the measurement engine 316 provides the one or more characteristics as the measured outer retinal thickness attribute for the adjacent area. The procedure 700*b* then advances to an end block and terminates.

Another non-limiting example of an attribute that may be useful in generating predicted enlargement rates is a choriocapillaris flow deficit. One of ordinary skill in the art will recognize that techniques are available for measuring choriocapillaris flow deficits from swept-source OCT angiography (SS-OCTA) images, such as those described in Thulliez, M., Zhang, Q., Shi, Y., Zhou, H., Chu, Z., de Sisternes, L., Durbin, M. K., Feuer, W., Gregori, G., Wang, R. K., & Rosenfeld, P. J. (2019); Correlations between Choriocapillaris Flow Deficits around Geographic Atrophy and Enlargement Rates Based on Swept-Source OCT Imaging; *Ophthalmology. Retina,* 3(6), 478-488; https://doi.org/10.1016/j.oret.2019.01.024, the entire disclosure of which is hereby incorporated by reference herein for all purposes.

Briefly, detection of angiographic flow information may be achieved using the complex optical microangiography ($OMAG^C$) technique. Choriocapillaris (CC) en face flow images may be generated by applying a 15 μm thick slab with the inner boundary located 4 μm under the Bruch's membrane 106. Retinal projection artifacts may be removed prior to compensating the CC en face flow images for signal attenuation caused by overlying structures such as RPE abnormalities including drusen, hyperreflective foci, and/or RPE migration. Compensation may be achieved by using the inverted images that corresponded to the CC en face structural images. The CC images may then undergo thresholding to generate CC flow deficit (FD) binary maps. Small areas of CC FD (e.g., CC FDs with a diameter smaller than 24 μm) may be removed as representing physiological FDs and speckle noise before final CC FD calculations.

Once CC FD areas have been labeled, various characteristics of the CC FD may be measured as attributes for an adjacent area. For example, a percentage of FDs (CC FD %) may be used, which is a ratio of the number of all pixels representing FDs divided by all of the pixels within the adjacent area. As another example, a mean or averaged FD size (MFDS) may be used, which is an average area of all isolated regions representing CC FDs within the adjacent area.

FIG. 8 is a non-limiting example embodiment of a machine learning model for performing a geographic atrophy segmentation task according to various aspects of the present disclosure. The illustrated machine learning model 802 is a U-net, though other machine learning models may use other architectures.

In the machine learning model 802, a 512×512 input layer accepts the three-channel false color image as input. As illustrated, the machine learning model 802 is shown as accepting either a one-channel image or a three-channel false color image as input. In some embodiments, the machine learning model 802 may be trained to accept a single-channel en face image for a slab extracted from the OCT data. For example, a subRPE slab extending from 64 μm below the Bruch's membrane 106 to 400 μm below the Bruch's membrane 106 may be extracted from the OCT data, and an en face image may be created using the sum projection for providing to a one-channel input layer of the machine learning model 802. Separate machine learning models 802 may be trained for the three-channel input layer and the one-channel input layer, and their performance may be compared.

In the contracting path (the left side of the machine learning model 802), the input layer is followed by two 3×3 convolutional layers with batch normalization and ReLU, a 2×2 MaxPool, two 3×3 convolutional layers with batch normalization and ReLU, another 2×2 MaxPool, two more 3×3 convolutional layers with batch normalization and ReLU, and a final 2×2 MaxPool. The bottom layer of the U-net includes two 3×3 convolutional layers, with batch normalization and ReLU, followed by a 2×2 up-convolution with ReLU. The results of the contracting path are copied and concatenated to the expansive path (the right side of the machine learning model 802).

In the expansive path of the machine learning model 802, a 3×3 convolutional layer with dropout, batch normalization, and ReLU is followed by a 3×3 convolution layer with batch normalization and ReLU and then a 2×2 up-convolution with ReLU. Next, a 3×3 convolution layer with dropout, batch normalization and ReLU is followed by another 3×3 convolution layer with batch normalization and ReLU and a 2×2 up-convolution with ReLU. Another 3×3 convolution layer with dropout, batch normalization and ReLU is executed, followed by another 3×3 convolution layer with batch normalization and ReLU and a 2×2 up-convolution with ReLU. Finally, a 3×3 convolution layer with dropout, batch normalization, and ReLU is followed by a 3×3 convolution layer with batch normalization and ReLU, and then a 1×1 convolution layer with a sigmoid activation function produces the segmented output.

Example: Segmentation Model Training and Testing

The following description describes a non-limiting example of a process of training a machine learning model 802 that was used to study the performance of the machine learning model 802. One of ordinary skill in the art will recognize that the example training steps described below should not be seen as limiting, and that in some embodiments, other steps (including but not limited to training data generated, selected, and organized using other techniques; different initializers, optimizers, evaluation metrics, and/or loss functions; and different settings for various constants and numbers of epochs) may be used.

Two machine learning models 802 were trained using the illustrated architecture but different input layers: one with a three-channel input layer to accept the false color images based on the OAC data as described above, and another with a one-channel input layer to accept the en face images of the subRPE slab from the OCT data. The en face images of the subRPE slab from the OCT data have been used in previous studies, and are being used with the novel machine learning model 802 in the present study to both show the superiority of the machine learning model 802 independent of the images used, and also to provide an apples-to-apples comparison to illustrate the superiority of the use of the described false color images based on OAC data compared to the previously used en face subRPE slab images generated from OCT data.

Training data was created and stored in the image data store 308 by manually annotating areas of geographic atrophy in the en face images of the subRPE slab from the OCT data, referencing B-scans, and was retrieved from the image data store 308 by the training engine 318 to conduct the training process.

Training used 80% of all eyes, and testing used 20% of the eyes. Within the training cases, an 80:20 split between training and validation was applied, partitioned at the eye level. Cases were shuffled and the set division was random. The learning rate, dropout, and batch normalization hyperparameters for the training process were tuned on the validation set using grid search. Data augmentation with zoom, shear, and rotation was used, and a batch size of 8 was used. For each 3×3 convolution layer, the He normal initializer was used for kernel initialization. The Adam optimizer was used and the model evaluation metric was defined as the soft DSC (sDSC). The loss function was the sDSC loss:

$$L_{sDSC} = 1 - \frac{2\sum_{i=1}^{N} p_i g_i + s}{\sum_{i=1}^{N} p_i^2 + \sum_{i=1}^{N} g^{i^2} + s}$$

where Nis the number of all pixels, $p_i$ and $g_i$ represent the ith pixel on the prediction and ground truth image respectively, and s is a smoothing constant set as 0.0001 to avoid dividing by zero. Each model was trained with 200 epochs with a patience for early stopping of 50 epochs, and the model with the best metric was saved in the model data store 320. The models were implemented in Keras using Tensorflow as the backend, and training was performed with a 16 GB NVIDIA Tesla P100 GPU through Google Colab.

To evaluate the performance of the trained models, DSC, area square-root difference (ASRD), subject-wise sensitivity, and specificity were calculated on the testing set:

$$DSC = \frac{2TP}{2TP + FP + FN}$$

$$\text{Sensitivity} = \frac{TP}{TP + FN}$$

$$\text{Specificity} = \frac{TN}{TN + FP}$$

where TP denotes true positive, TN denotes true negative, FP denotes false positive, and FN denotes false negative. TP, FP, and FN in the DSC equation represent pixel level information, and TP, TN, FP, and FN in the sensitivity and specificity equations represent eye level information. A threshold of 0.5 was used to binarize the probability map from the model's prediction output. An image with any geographic atrophy pixels is classified as having geographic atrophy.

To further compare the identified GA regions, total area and square-root area measurements of GA were calculated for both ground truth and model outputs. A square-root transformation was applied to calculate the size and growth of geographic atrophy since this strategy decreases the influence of baseline lesion size on the test-retest variability and on the growth of geographic atrophy. The paired t-test was used to compare model outputs using the false color images based on the OAC data and the subRPE images based on the OCT data. Pearson's linear correlation was used to compare the square-root area of the manual and automatic segmentations, and Bland-Altman plots were used to analyze the agreement between the square-root area of the manual and automatic segmentations. P values of $<0.05$ were considered to be statistically significant.

In total, 80 eyes diagnosed with geographic atrophy secondary to nonexudative AMD and 60 normal eyes with no history of ocular disease, normal vision, and no identified optic disc, retinal, or choroidal pathologies on examination were included in the study. All cases were randomly shuffled such that 51 geographic atrophy eyes and 38 normal eyes were used for training, 13 geographic atrophy eyes and 10 normal eyes were used for validation, and 16 geographic atrophy eyes and 12 normal eyes were used for testing. In the training dataset, 22 out of these 51 eyes had three scans from three visits and these scans were added into the training set for data augmentation. Eyes in the validation and testing set only had one scan.

Both models were trained using the same learning rate of 0.0003 and the same batch normalization momentum of 0.1 with the scale set as false. A dropout of 0.3 was used for the machine learning model 802 trained to process the false color images and a dropout of 0.5 was used for the machine learning model 802 trained to process the single-channel images based on the OCT data. All hyperparameters were tuned on the validation set. Each model was trained with 200 epochs and their specific sDSC for training, validation, and testing are given in the following table:

| Soft DICE | False Color Image From OAC Data | SubRPE Slab From OCT Data |
|---|---|---|
| Training | 0.948 | 0.951 |
| Validation | 0.931 | 0.922 |
| Testing | 0.944 | 0.897 |

A series of evaluation metrics were quantified on the testing cases for each trained model, and their specific values are tabulated in the following table:

| | False Color Image From OAC Data | SubRPE Slab From OCT Data |
|---|---|---|
| DSC (geographic atrophy eyes) | 0.940 ± 0.032 | 0.889 ± 0.056 |
| Sensitivity | 100% | 100% |
| Specificity | 100% | 100% |

For testing, the model outputs, geographic atrophy probability maps (0-1), were binarized with a threshold of 0.5. DSC was calculated for each individual image and the mean and standard deviation (SD) were reported in the table above for each model. In the 16 geographic atrophy eyes in the testing set, the machine learning model 802 operating on the false color images from the OAC data significantly outperformed the machine learning model 802 operating on the subRPE slab from the OCT data (p=0.03, paired t-test). Both models achieve 100% sensitivity and 100% specificity in identifying geographic atrophy subjects from normal subjects.

Figure 9A:
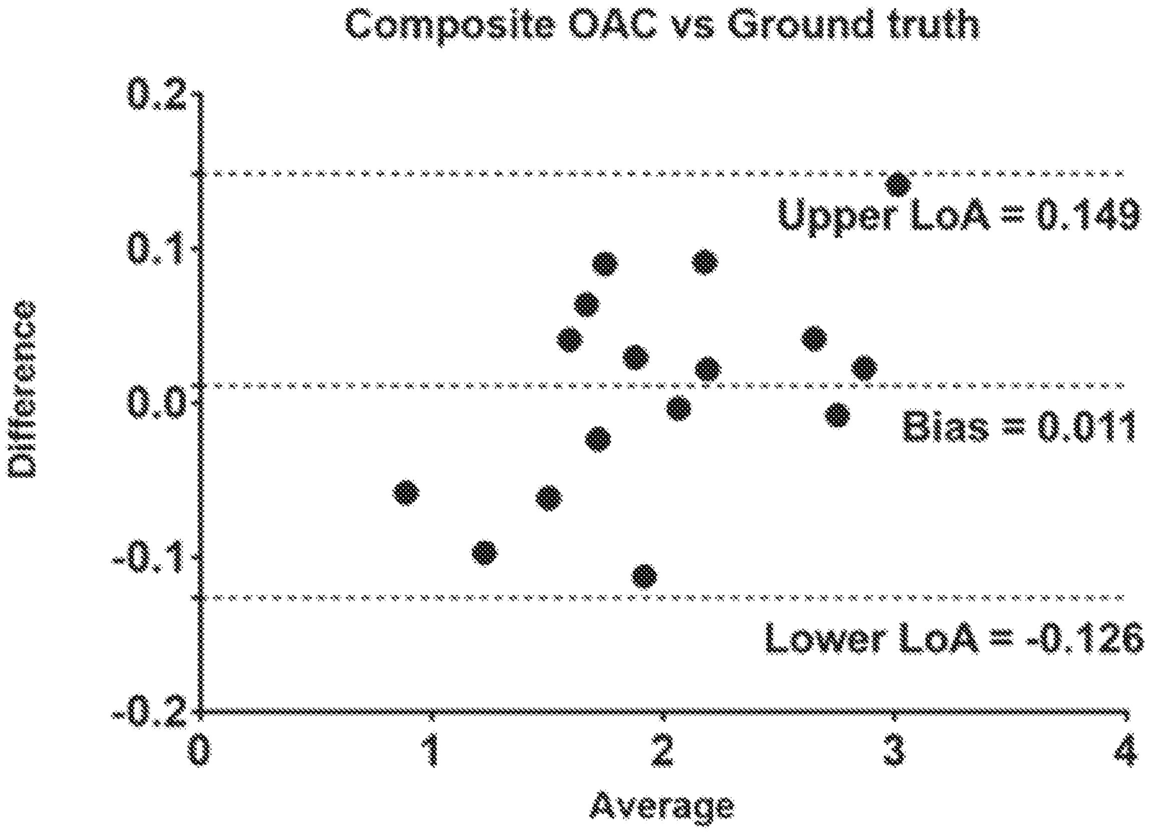
FIG. 9A to FIG. 9D include Bland-Altman plots and Pearson's correlation plots for testing of two non-limiting example machine learning models according to various aspects of the present disclosure.
Figure 9B:
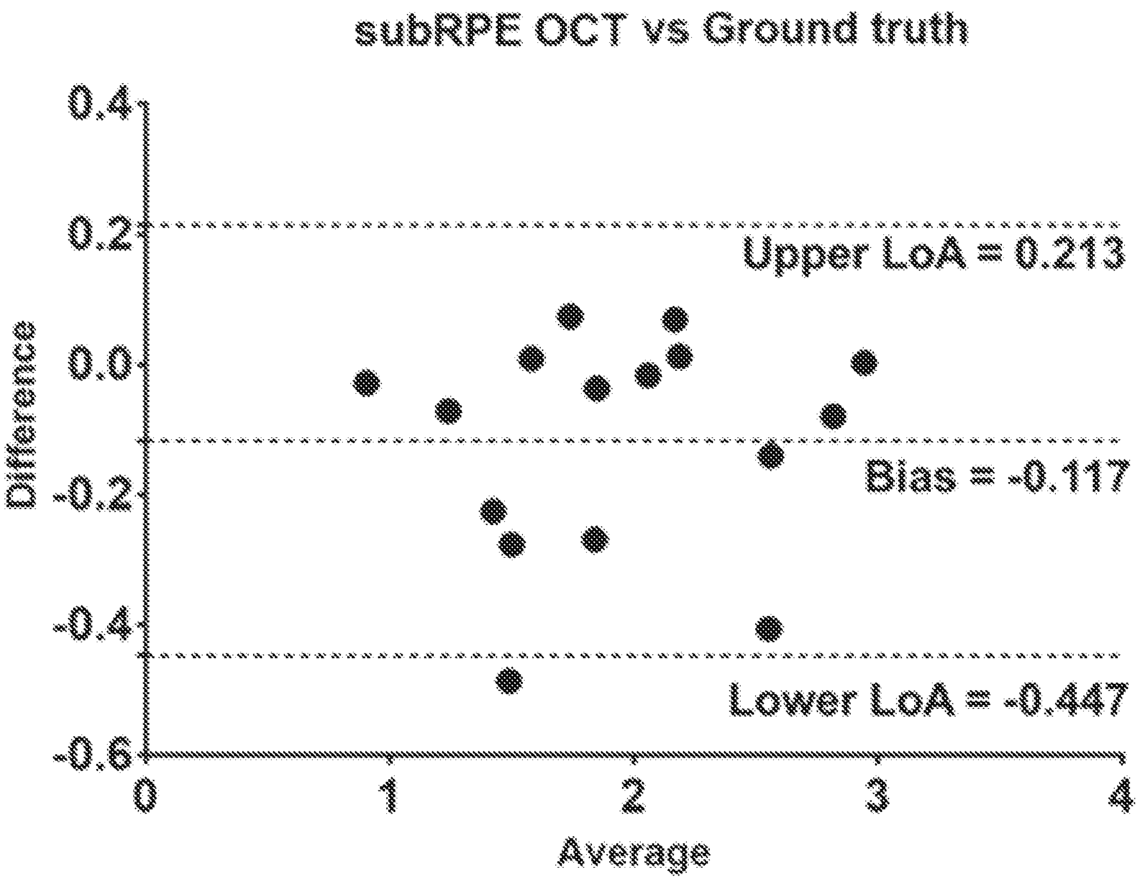
Figure 9C:
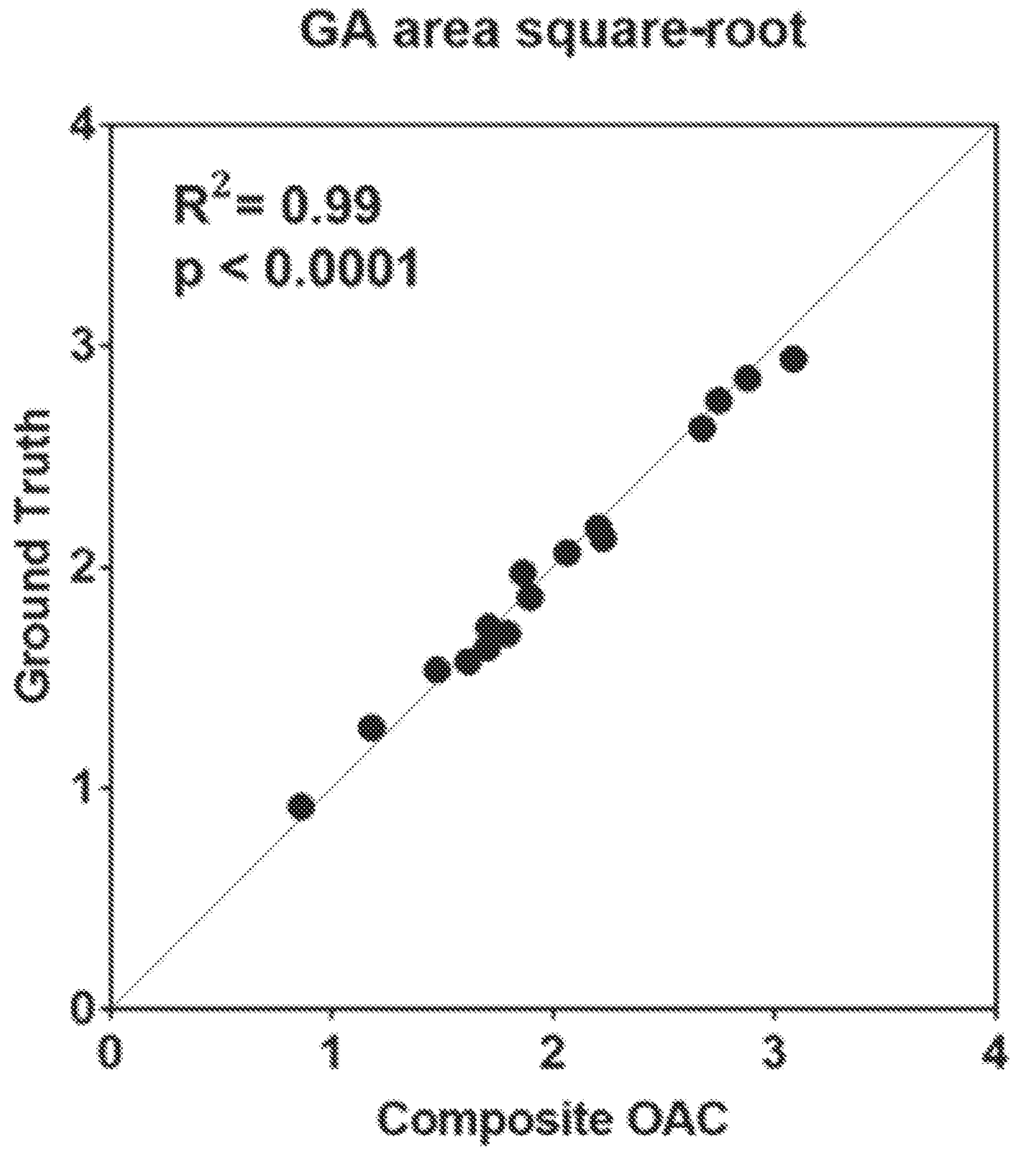
Figure 9D:
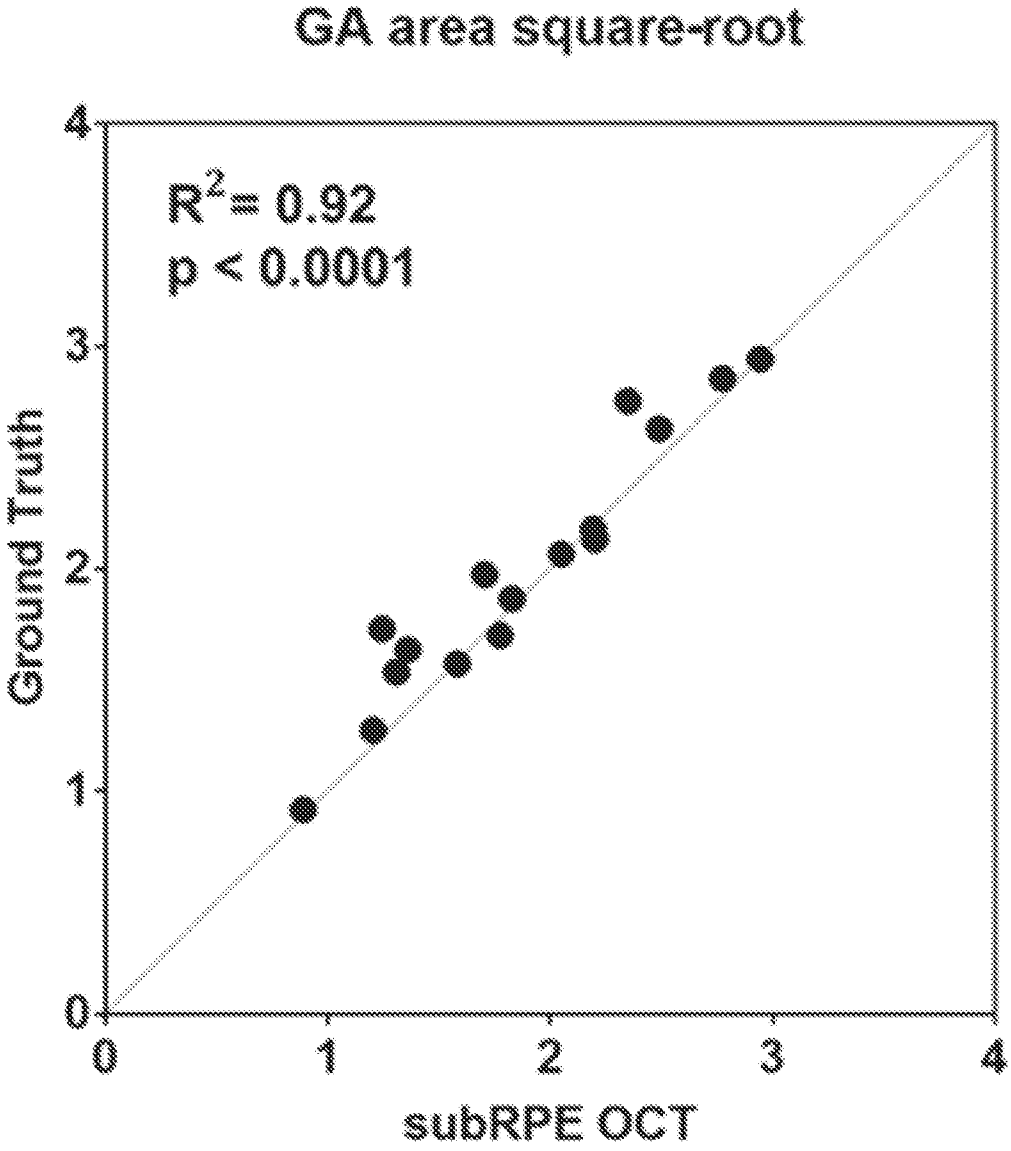
Figure 10A:
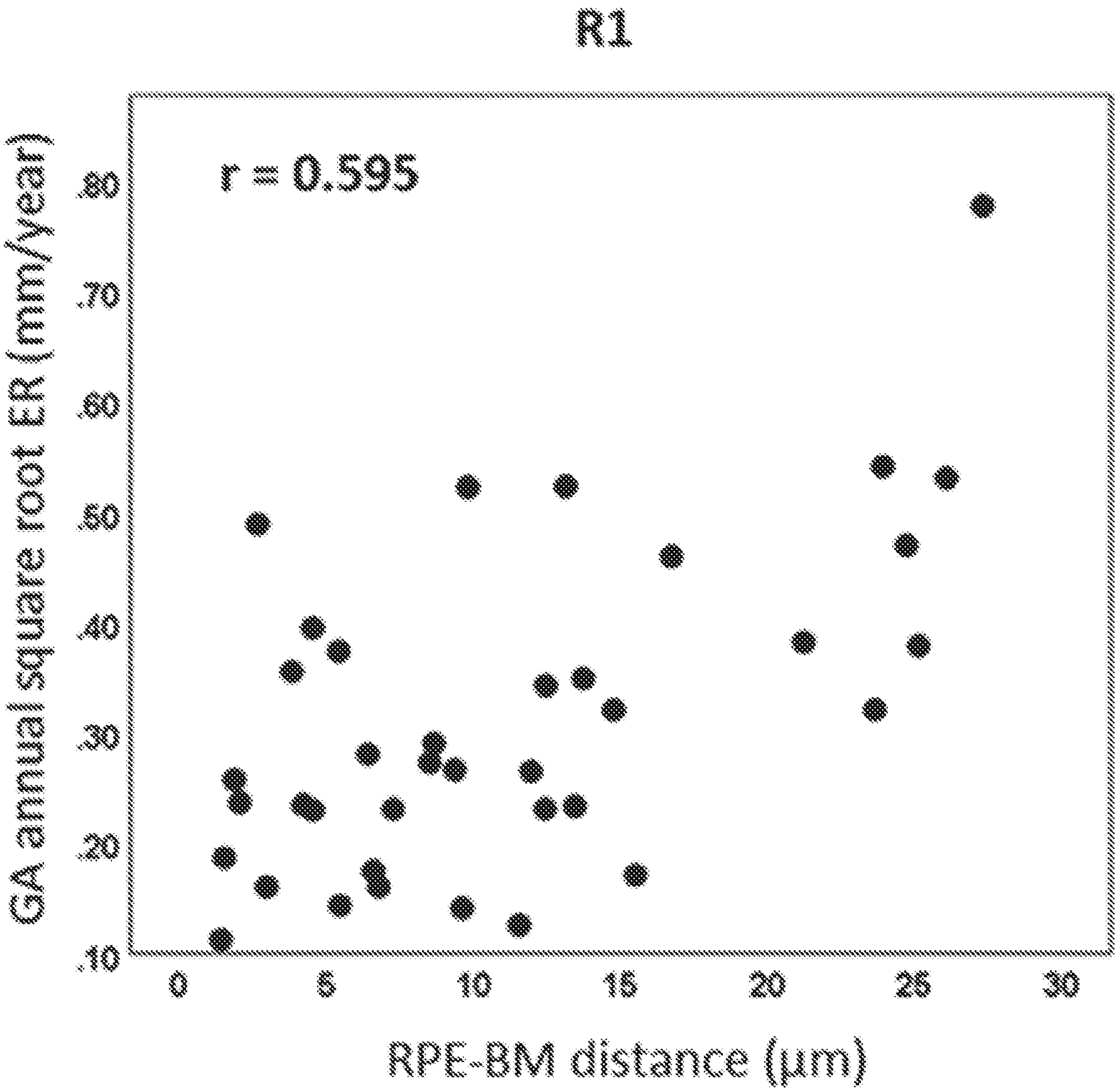
FIG. 10A to FIG. 10E include scatter plots that show correlations between RPE-BM distances in various adjacent areas to measured enlargement rates when testing a non-limiting example embodiment of the present disclosure.
Figure 10B:
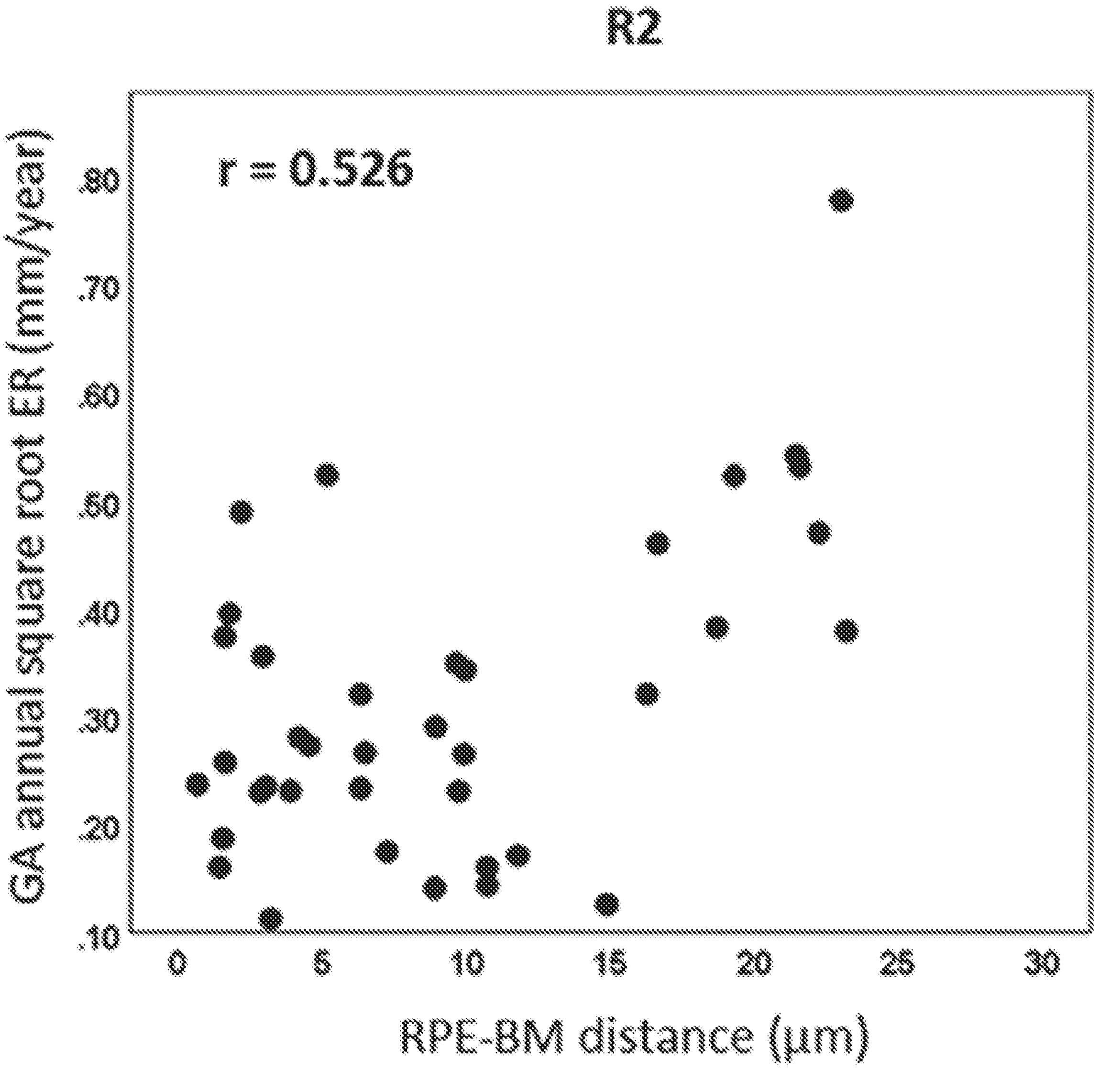
Figure 10C:
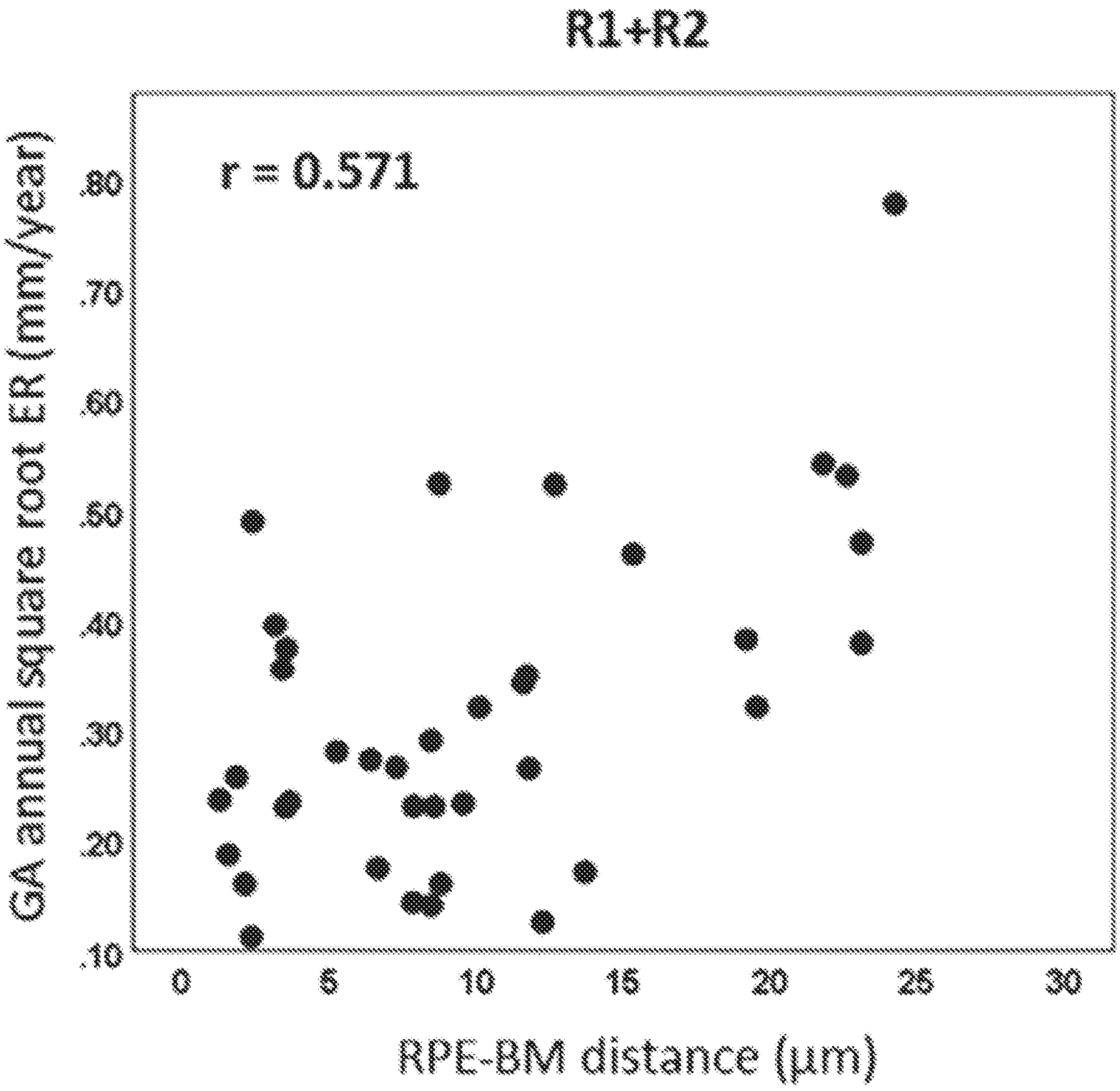
Figure 10D:
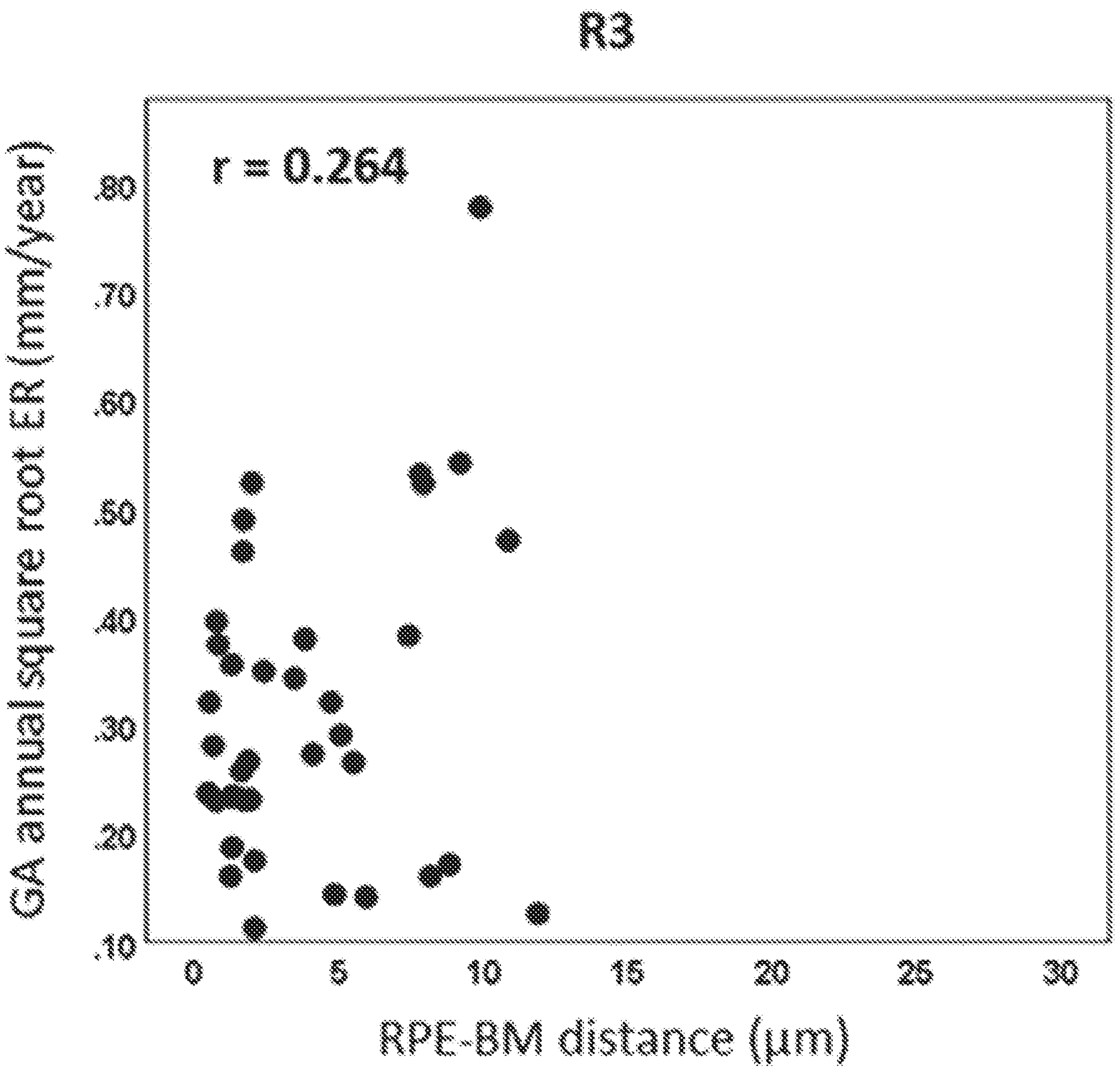
Figure 10E:
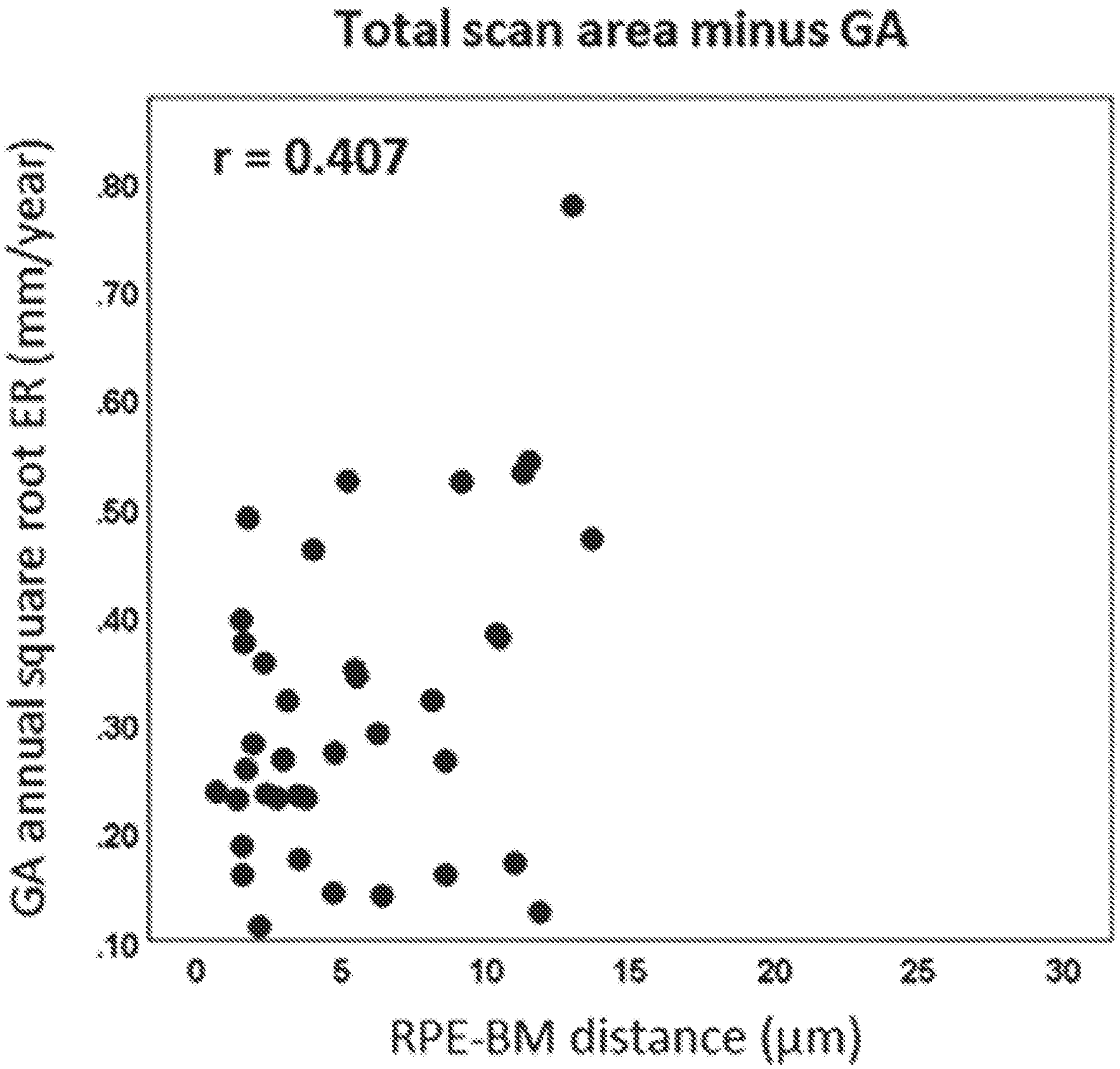

To further compare the quantification of segmentation generated by our models with the ground truth, the geographic atrophy square-root area was calculated for all geographic atrophy cases in the test set. FIG. 9A to FIG. 9D show the Bland-Altman plots and Pearson's correlation plots of both proposed models. FIG. 9A illustrates a Bland-Altman plot of geographic atrophy (GA) square-root area generated by the machine learning model 802 operating on the false color images from the OAC data compared with ground truth. FIG. 9B illustrates a Bland-Altman plot of GA square-root area generated by the machine learning model 802 operating on the subRPE slab from the OCT data compared with ground truth. FIG. 9C illustrates a Pearson's correlation plot of GA square-root area generated by the machine learning model 802 operating on the false color images from the OAC data with ground truth. FIG. 9D illustrates a Pearson's correlation plot of GA square-root area generated by the machine learning model 802 operating on the subRPE slab from the OCT data with ground truth. All units of axes are in mm. LoA is the limit of agreement.

Geographic atrophy square-root area segmented by both models showed significant correlation with ground truth ($R2=0.99$ for OAC data model and $R2=0.92$ for OCT data model, both $p<0.0001$). Both model outputs also showed satisfactory agreement with the ground truth. The machine learning model 802 operating on the false color images from the OAC data resulted in a smaller bias of 11 μm while the machine learning model 802 operating on the subRPE slab from the OCT data resulted in a larger bias of 117 μm, compared with the ground truth.

Using the same model architecture, the same hyper-parameter tuning process, and the same patients' OCT scans, the above demonstrates a significantly higher agreement with the ground truth by using the machine learning model 802 trained to use the false color images generated from OAC data than by using subRPE images generated from OCT data. For all 28 eyes in the testing sets, both models successfully identified eyes with geographic atrophy from normal eyes. For the 16 eyes with geographic atrophy in the testing sets, the machine learning model 802 trained to process false color images generated from OAC data achieved a mean DSC of 0.940 and a SD of 0.032, significantly higher than the other model with a mean DSC of 0.889 and a SD of 0.056 ($p=0.03$, paired t-test), respectively. For geographic atrophy square-root area measurements, the machine learning model 802 trained to process false color images generated from OAC data achieved a stronger correlation with the ground truth than the other model ($r=0.995$ vs $r=0.959$, $r^2=0.99$ vs $r^2=0.92$), as well as a smaller mean bias (11 μm vs 117 μm).

That said, using the machine learning model 802 with the subRPE images generated from SS-OCT data, a DSC of 0.889±0.056 was obtained, similar to what were used in previous SD-OCT studies. Though different datasets were used in different studies and direct comparisons of testing DSC values are somewhat unfair, the machine learning model 802 trained on the OCT data achieved a segmentation accuracy that was similar to these previous studies. That said, the machine learning model 802 trained to process false color images generated from OAC data achieved a significantly higher segmentation accuracy (0.940±0.032) compared with the similar machine learning model 802 using OCT subRPE images. This is a fair comparison since the same volumetric OCT data was used to generate the en face images for input in the models, though the OAC data undergoes further preprocessing. It should also be noted that though the structure of the machine learning model 802 is simpler compared to previously published studies, the segmentation accuracy provided by the machine learning model 802 in terms of DSC is similar to or superior to what were reported in previous studies, possibly due to the use of the enhanced contrast of geographic atrophy produced by using the OAC.

Example Prediction One: RPE-BM Distance

In some embodiments, the distance between the retinal pigment epithelium 104 and the Bruch's membrane 106 (RPE-BM distance) may be one of the attributes measured within the adjacent area, and may be used for prediction of progression of geographic atrophy. In this example, a multiple linear regression model that accepts RPE-BM distance as well as choriocapillaris flow deficit percentage (CC FD %) serves as the prediction model for generating the predicted enlargement rate.

In a study, Pearson correlation was used to evaluate the relationships between the OAC-measured RPE-BM distances and the normalized annual square root enlargement rates of geographic atrophy, as well as the relationship between previously determined choriocapillaris flow deficit percentages (CC FD %) and the RPE-BM distance of the same eyes. To assess the combined effects of RPE-BM distance and CC FD % on predicting geographic atrophy growth, a multiple linear regression model was calculated using RPE-BM distance and CC FD % as variables and the normalized annual square root enlargement rate of geographic atrophy as the outcome. A P value of <0.05 was considered to be statistically significant.

A total of 38 eyes from 27 subjects diagnosed with geographic atrophy secondary to nonexudative AMD were included in the study. The relationship between the enlargement rate of geographic atrophy in these eyes and the surrounding CC FD % s and underlying choroidal parameters were previously determined in these eyes. The techniques illustrated in FIG. 4 and FIG. 6 were used to process the OCT data, and the technique illustrated in FIG. 7A was used to measure the RPE-BM distance.

For the 38 eyes, the annual square root enlargement rates ranged from 0.11 mm/y to 0.78 mm/y, with a mean of 0.31 mm/y and a standard deviation of 0.15 mm/y. The RPM-BM distance calculated using the technique illustrated in FIG. 7A was found to significantly correlate with the annual geographic atrophy square root enlargement rates. The following table shows specific correlation (r) and significance (P) values for each adjacent area, and RPE-BM distances measured in each adjacent area. RPE-BM distances in all adjacent areas except R3 (the area from 600 μm outside of the geographic atrophy area to the edge of the scan) showed a significant correlation with geographic atrophy annual square root enlargement rates. R1 (the 1-degree rim region) showed the strongest correlation among all adjacent areas, although the significant correlations in the other adjacent areas were not significantly different from each other. These correlations are shown as scatter plots in FIG. 10A to FIG. 10E.

| Region of Interest | RPE-BM Distance, Mean ± SD (μm) | Pearson r, P Value |
|---|---|---|
| R1 (0-300 μm) | 11.09 ± 7.74 | r = 0.595, P < .001 |
| R2 (300-600 μm) | 9.33 ± 7.14 | r = 0.526, P < .001 |
| R1 + R2 (0-600 μm) | 9.88 ± 6.90 | r = 0.571, P < .001 |
| R3 (total scan area minus GA, R1, R2) | 3.92 ± 3.33 | r = 0.264, P < .110 |
| Total scan area minus GA | 5.53 ± 3.89 | r = 0.407, P < .011 |

A significant correlation between the annual square root enlargement rates of geographic atrophy and CC FD % in these same eyes had previously been determined. To further understand the relationships between CC FD % and RPE-BM distances, Pearson's correlation was performed between these two metrics in each adjacent area, and no significant correlations were found in any adjacent area (all Pearson $r<0.083$, all $P>0.622$). Therefore, CC FD % in the total scan area minus GA (strongest correlation for CC FD %) and RPE-BM distance in R1 (strongest correlation for RPE-BM distance) were combined to fit a multiple linear regression model to predict annual square root enlargement rates for geographic atrophy. This prediction model was as follows:

$$\text{predicted annual square root enlargement rate} = 0.019 * \text{CC FD\%} + 0.0083 * \text{RPE-BM distance} - 0.0795$$

Figure 11:
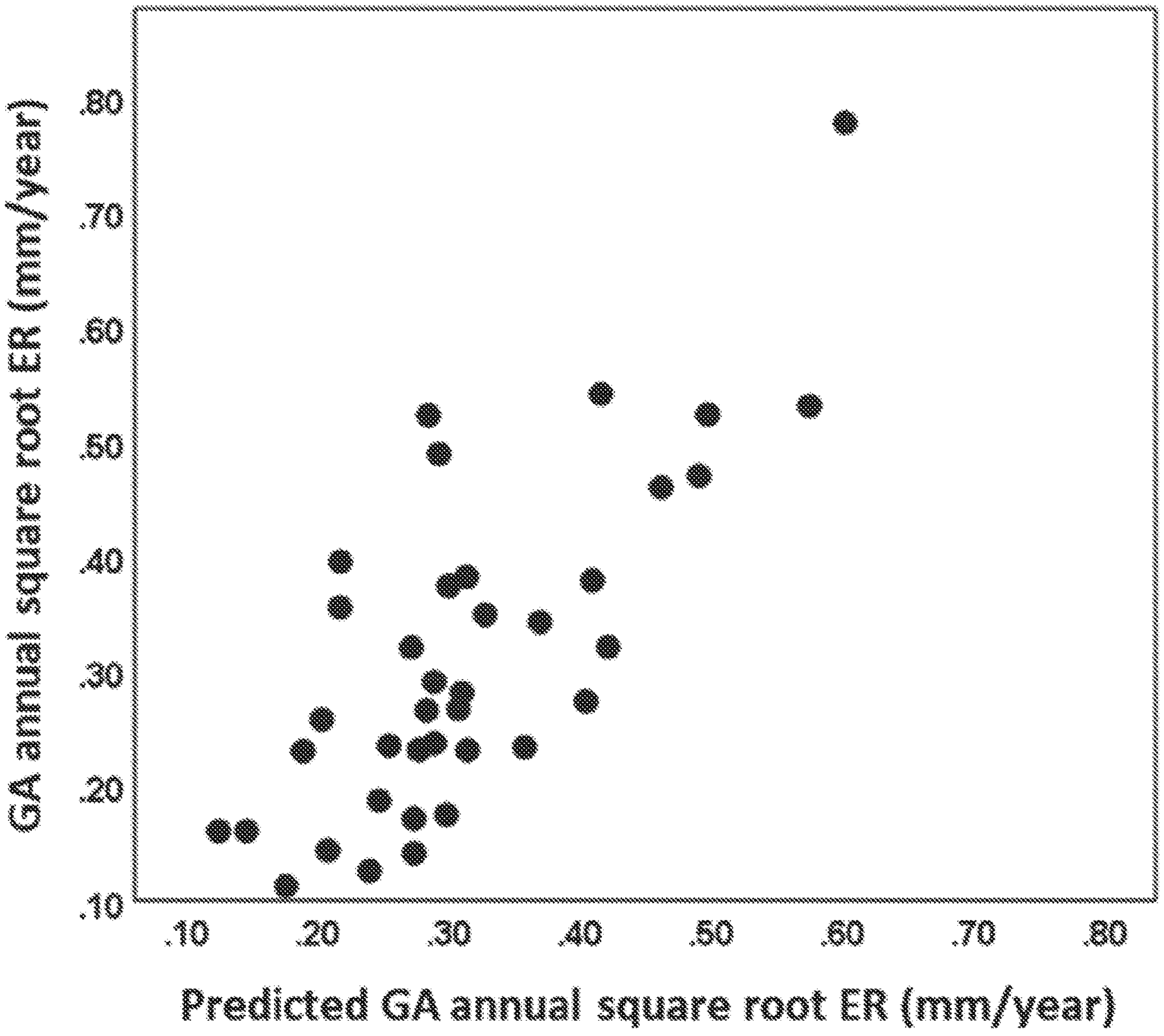
FIG. 11 includes a scatter plot of measured annual square root enlargement rate of geographic atrophy against predictions generated by a non-limiting example embodiment of a prediction model according to various aspects of the present disclosure.
Figure 12A:
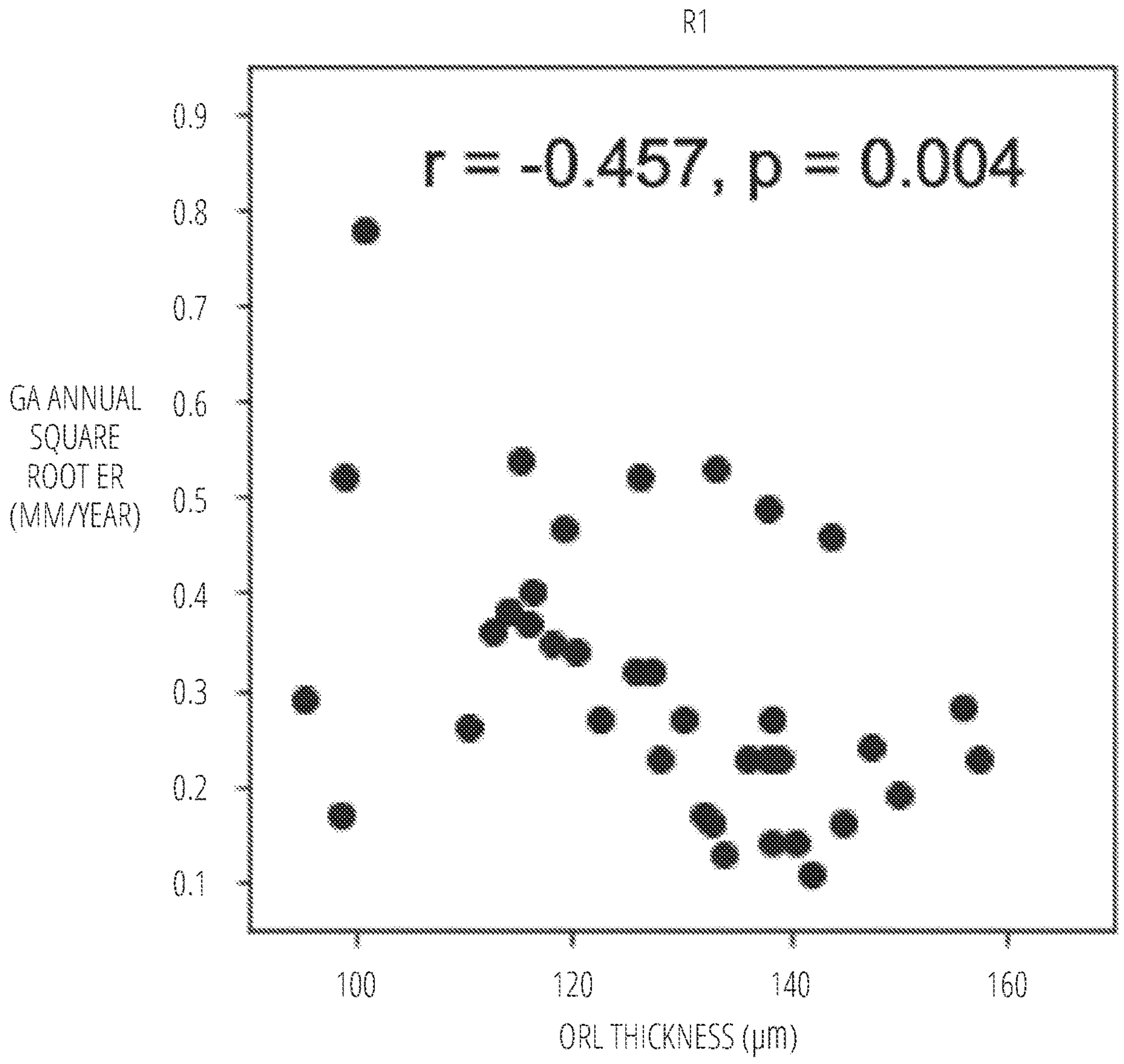
FIG. 12A to FIG. 12E include scatter plots that show correlations between outer retinal thickness in various adjacent areas to measured enlargement rates when testing a non-limiting example embodiment of the present disclosure.
Figure 12B:
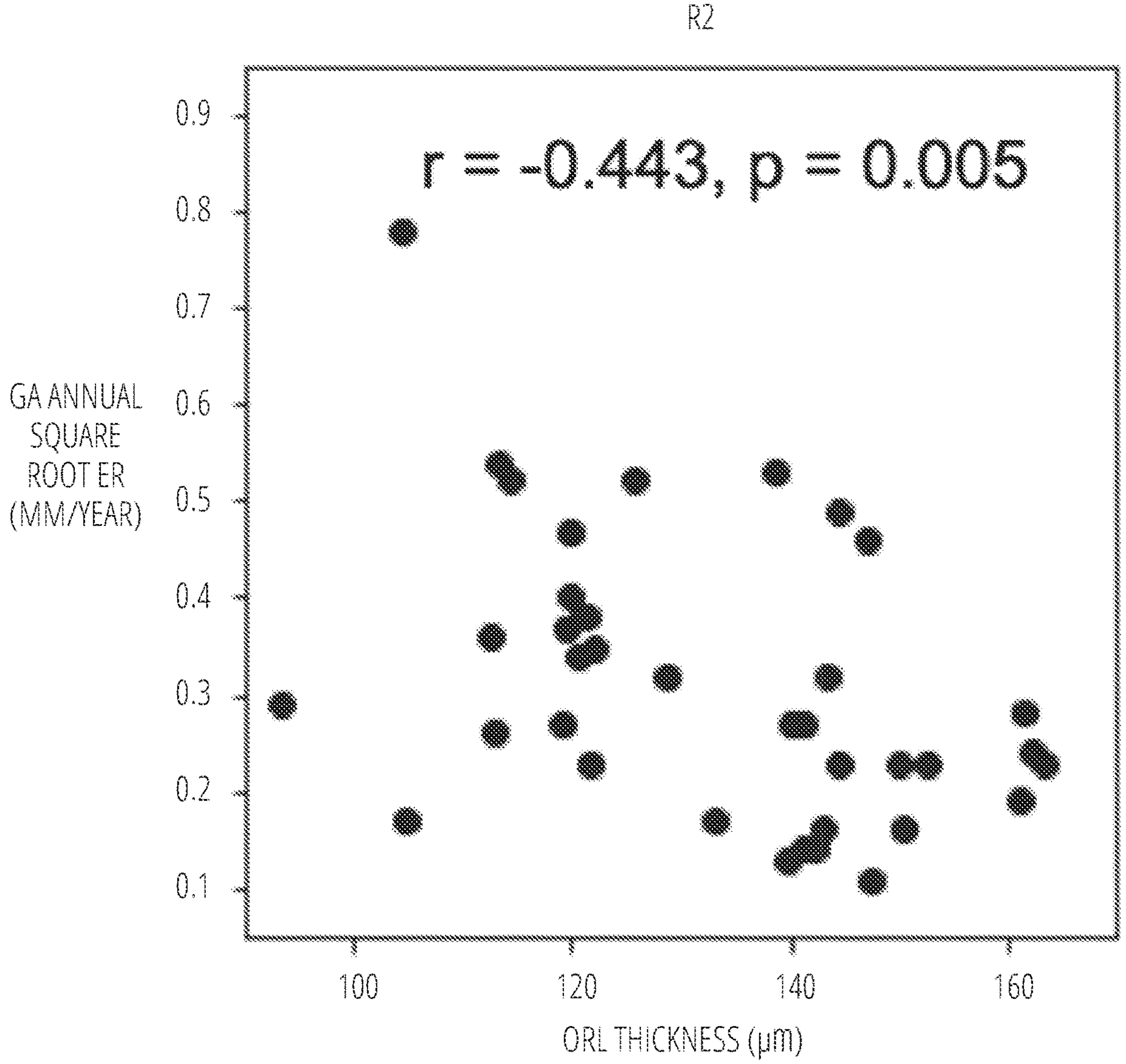
Figure 12C:
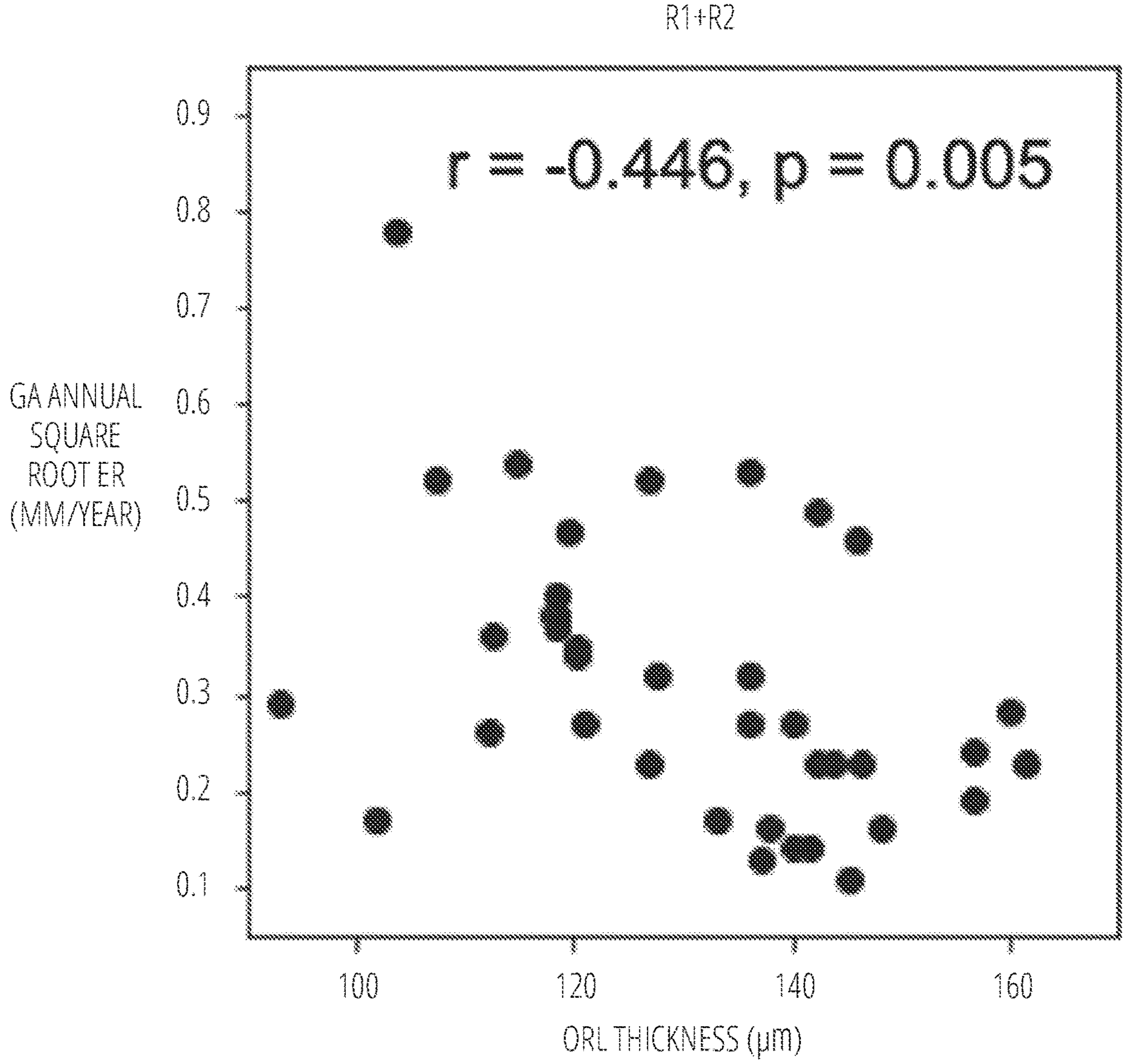
Figure 12D:
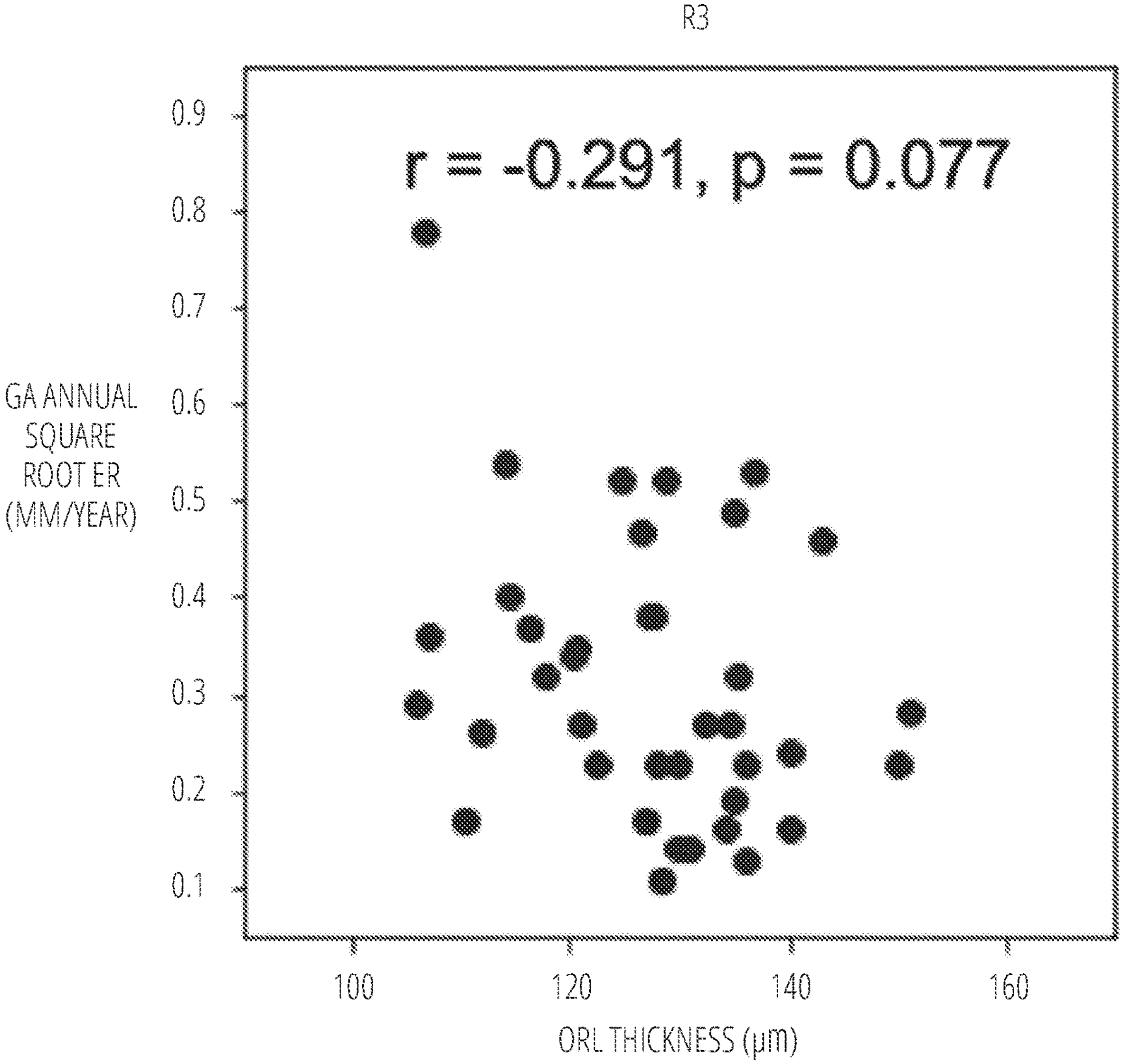
Figure 12E:
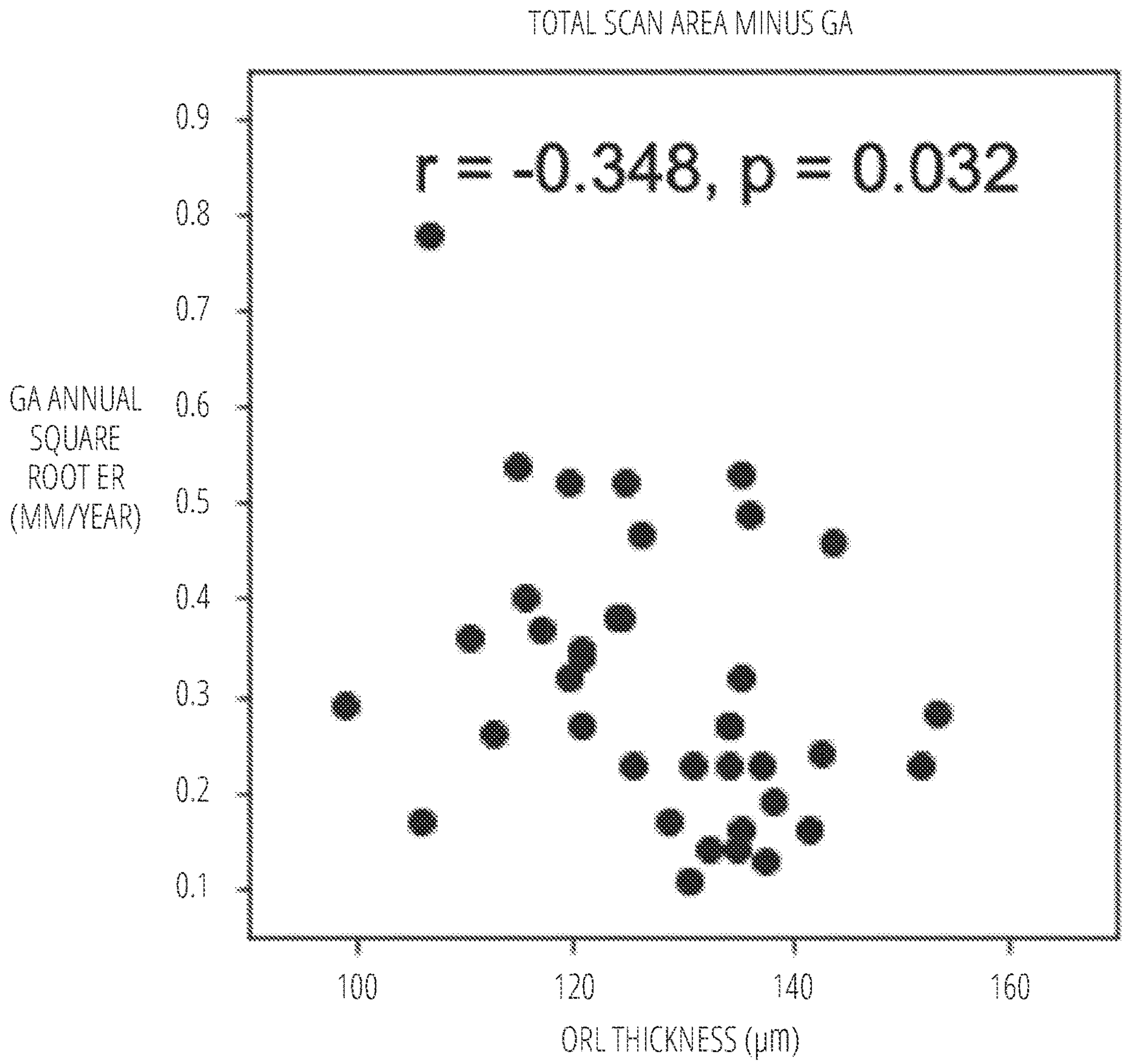

Using these variables, this prediction model resulted in a combined r of 0.75 and $r^2$ of 0.57. FIG. 11 illustrates a scatter plot of measured annual square root enlargement rate of geographic atrophy against the predictions generated by this prediction model for all 38 eyes.

Example Prediction Two: Outer Retinal Thickness

In some embodiments, the outer retinal layer (ORL) thickness may be one of the attributes measured within the adjacent area, and may be used for prediction of progression of geographic atrophy. In this example, a multiple linear regression model that accepts ORL thickness, as well as the RPE-BM distance and choriocapillaris flow deficit percentage (CC FD %) discussed in Example One, serves as the prediction model for generating the predicted enlargement rate.

In a study of the same eyes as Example One, Pearson's correlation was used to evaluate the relationships between the ORL thickness (measured using the procedure 700*b* illustrated in FIG. 7B) and the normalized annual square root enlargement rates of geographic atrophy, as well as the relationship between the CC FD % and the RPE-BM distances discussed in Example One for the same eyes. A multiple-parameter linear regression model was established for the prediction model using the CC FD %, the RPE-BM distance, and the ORL thickness measurements as variables and the normalized annual square root enlargement rates of geographic atrophy as the outcome. This prediction model was as follows:

$$\text{predicted annual square root enlargement rate} = 0.019 * \text{CC FD\%} + 0.007 * \text{RPE-BM distance} - 0.002 * \text{ORL thickness} + 0.246$$

A P value of <0.05 was considered to be statistically significant. The below table shows the detailed correlations (r) and significance values (P) for each adjacent area and the averaged ORL thickness in each sub-region. The ORL thickness measurements in all adjacent areas except for R3 were shown to have significant negative correlations with the annual square root enlargement rate of geographic atrophy. The R1 region had the strongest negative correlation (r=−0.457, P=0.004) among all of the adjacent areas. The correlations in all adjacent areas are shown as scatter plots in FIG. 12A to FIG. 12E.

| Region of Interest | ORL Thickness, Mean ± SD (μm) | Pearson r, P Value |
|---|---|---|
| R1 (0-300 μm) | 127.66 ± 15.67 | r = −0.457, P = .004 |
| R2 (300-600 μm) | 132.75 ± 17.63 | r = −0.443, P = .005 |
| R1 + R2 (0-600 μm) | 130.76 ± 16.70 | r = −0.446, P = .005 |
| R3 (total scan area minus GA, R1, R2) | 127.33 ± 11.25 | r = −0.291, P = .077 |
| Total scan area minus GA | 127.83 ± 12.29 | r = −0.348, P = .032 |

Figure 13:
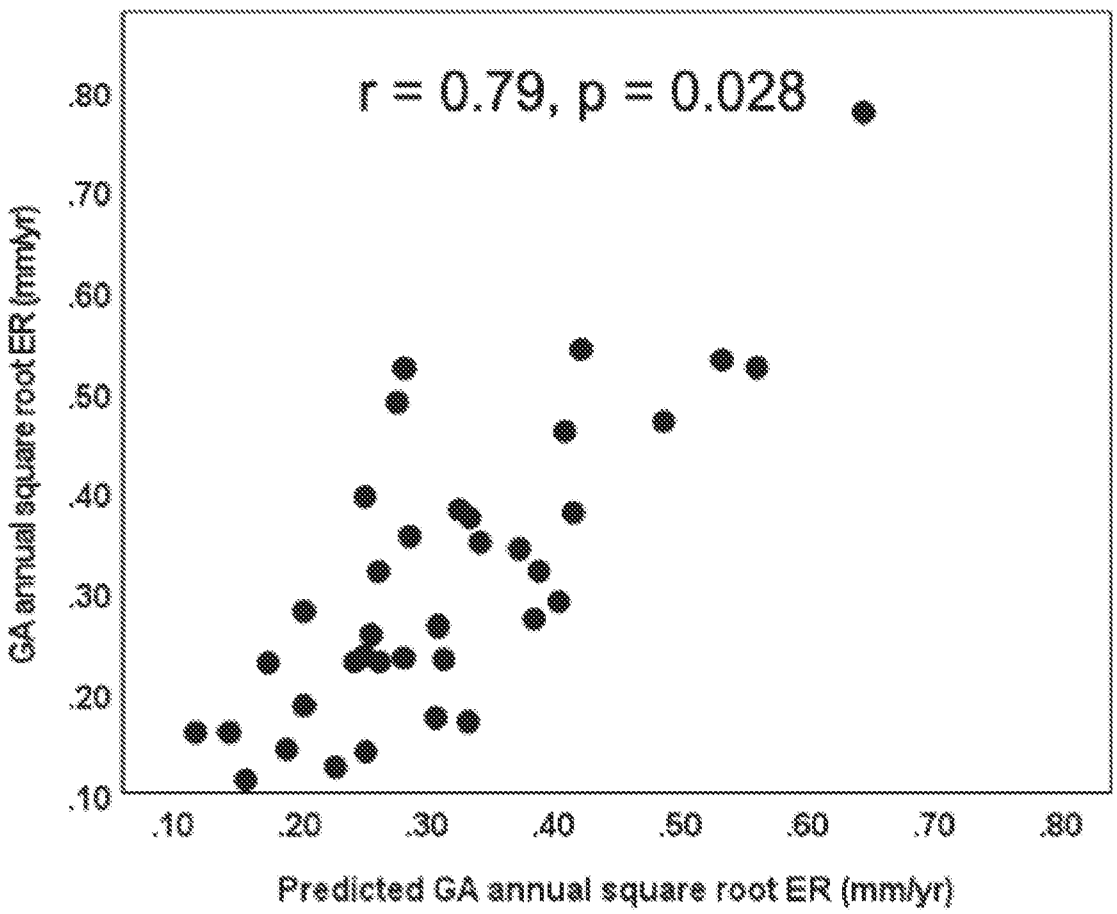
FIG. 13 includes a scatter plot of measured annual square root enlargement rate of geographic atrophy against predictions generated by another non-limiting example embodiment of a prediction model according to various aspects of the present disclosure.

Adding the ORL thickness measurement in R1 (the strongest correlation with annual square root enlargement rate of geographic atrophy) to the prediction model that already considered CC FD % and RPE-BM thickness provided an improvement in r to 0.79 ($r^2$=0.62). The predicted enlargement rates calculated by this prediction model, with a mean±SD of 0.32 mm/year±0.12 mm/year and 95% confidence intervals ranging from 0.277 mm/year to 0.357 mm/year, significantly correlated with (P=0.028) the measured annual square root enlargement rates of geographic atrophy (mean±SD of 0.31 mm/year±0.15 mm/year, with 95% confidence intervals ranging from 0.267 mm/year to 0.368 mm/year). FIG. 13 is a scatter plot that illustrates the measured enlargement rates versus the predicted enlargement rates using the model from Example Two. Adding the ORL thickness into the model increased the explained variability of annual square root enlargement rates of geographic atrophy by about 6%.

A Pearson's correlation was further performed between CC FD % and ORL thickness and between RPE-BM distance and ORL thickness in each adjacent area. No significant correlations were found in any adjacent areas between CC FD % and ORL thickness, but a significant correlation was found in the R1 region between RPE-BM distance and ORL thickness (Pearson's r=−0.398, P=0.013).

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of automatically predicting progression of age-related macular degeneration, the method comprising:

receiving, by an image analysis computing system, optical coherence tomography data (OCT data);

determining, by the image analysis computing system, an optical attenuation coefficient for each pixel of the OCT data to create optical attenuation coefficient data (OAC data) corresponding to the OCT data;

determining, by the image analysis computing system, an area exhibiting geographic atrophy based on at least one of the OCT data and the OAC data;

measuring, by the image analysis computing system, one or more attributes within an adjacent area that is adjacent to the area exhibiting geographic atrophy; and determining, by the image analysis computing system, a predicted enlargement rate based on the one or more attributes within the adjacent area;

wherein measuring one or more attributes within the adjacent area that is adjacent to the area exhibiting geographic atrophy includes at least one of:

measuring a distance between a retinal pigment epithelium (RPE) and a Bruch's membrane (BM) within the adjacent area;

measuring an outer retinal layer thickness within the adjacent area; or measuring choriocapillaris flow deficits within the adjacent area.

2. The computer-implemented method of claim 1, further comprising:

providing, by the image analysis computing system, the predicted enlargement rate for use in at least one of a diagnosis, a determination of an appropriate treatment, and an evaluation of an applied treatment.

3. The computer-implemented method of claim 1, wherein measuring the distance between the RPE and the BM includes identifying a pixel above the BM having a maximum optical attenuation coefficient value.

4. The computer-implemented method of claim 1, wherein measuring the one or more attributes within the adjacent area includes determining a mean and a standard deviation of the measured distance between the RPE and the BM within the adjacent area.

5. The computer-implemented method of claim 1, wherein measuring the outer retinal layer thickness within the adjacent area includes:

determining a location of the retinal pigment epithelium (RPE) by identifying a pixel above the BM having a maximum optical coefficient value;

determining a location of an inner boundary of an outer plexiform layer (OPL); and measuring the distance between the location of the RPE and the OPL within the adjacent area.

6. The computer-implemented method of claim 1, wherein measuring the one or more attributes within the adjacent area includes determining a mean and a standard deviation of the outer retinal layer thickness within the adjacent area.

7. The computer-implemented method of claim 1, wherein measuring one or more attributes within the adjacent area that is adjacent to the area exhibiting geographic atrophy includes measuring the one or more attributes within:

a 1-degree rim region that extends from 0 μm to 300 μm outside the area exhibiting geographic atrophy;

an additional 1-degree rim region that extends from 300 μm outside the area exhibiting geographic atrophy to 600 μm outside the area exhibiting geographic atrophy;

a 2-degree rim region that extends from 0 μm to 600 μm outside the area exhibiting geographic atrophy;

a region that extends from 600 μm outside the area exhibiting geographic atrophy to an edge of the OAC data; and a region that extends from the area exhibiting geographic atrophy to the edge of the OAC data.

8. The computer-implemented method of claim 1, wherein determining the predicted enlargement rate based on the one or more attributes within the adjacent area includes providing the one or more attributes to a multiple linear regression model.

9. The computer-implemented method of claim 8, wherein providing the one or more attributes to the multiple linear regression model includes providing the measured distance between the RPE and the BM within the adjacent area and the measured choriocapillaris flow deficit within the adjacent area to the multiple linear regression model.

10. The computer-implemented method of claim 9, wherein providing the one or more attributes to the multiple linear regression model further includes providing the measured outer retinal layer thickness within the adjacent area to the multiple linear regression model.

11. The computer-implemented method of claim 1, wherein determining the area exhibiting geographic atrophy based on at least one of the OCT data and the OAC data includes:

extracting a subRPE slab from the OCT data to generate an en face OCT image; and at least one of:

providing the en face OCT image to a machine learning model trained to detect areas exhibiting geographic atrophy within en face OCT images; and presenting the en face OCT image to a user to receive manual annotations of areas exhibiting geographic atrophy within the en face OCT image.

12. A computer-implemented method of automatically detecting an area of an eye exhibiting geographic atrophy, the method comprising:

receiving, by an image analysis computing system, optical coherence tomography data (OCT data);

determining, by the image analysis computing system, an optical attenuation coefficient for each pixel of the OCT data to create optical attenuation coefficient data (OAC data) corresponding to the OCT data; and determining, by the image analysis computing system, an area exhibiting geographic atrophy based on the OAC data;

wherein determining the area exhibiting geographic atrophy based on the OAC data includes:

determining a location of a Bruch's membrane within the OAC data;

extracting a slab from the OAC data located above the Bruch's membrane;

generating an en face OAC maximum projection image for a slab from the OAC data located above the Bruch's membrane;

generating an en face OAC sum projection image for the slab;

generating an en face retinal pigment epithelium to Bruch's membrane distance map (RPE-BM distance map) for the slab;

generating an en face false color image for the slab by combining the en face OAC maximum projection image, the en face OAC sum projection image, and the en face RPE-BM distance map; and providing the en face false color image to a machine learning model trained to detect areas exhibiting geographic atrophy within en face false color images.

13. The computer-implemented method of claim 12, wherein determining the optical attenuation coefficient for each pixel of the OCT data to create OAC data corresponding to the OCT data includes calculating, for each pixel i, a value μ[i] that represents the OAC of the ith pixel, wherein:

$$\mu[i] = \frac{I[i]}{2\Delta\int_{i+1}^{\infty} I[i]}$$

wherein Δ is an axial size of each pixel;

wherein I[i] is a detected OCT signal intensity at the ith pixel; and wherein $$\int_{i+1}^{\infty} I[i]$$

is calculated by adding OCT signal intensities of all pixels beneath the ith pixel.

14. The computer-implemented method of claim 12, further comprising:

determining the location of the Bruch's membrane within the OAC data by:

providing the OCT data to a model configured to identify the Bruch's membrane within OCT data; and transferring the location of the Bruch's membrane identified within the OCT data to the corresponding OAC data.

15. The computer-implemented method of claim 8, wherein the machine learning model trained to detect areas exhibiting geographic atrophy within en face false color images is a U-net.

16. A non-transitory computer-readable medium having computer-executable instructions stored thereon that, in response to execution by one or more processors of an image analysis computing system, cause the computing system to perform actions comprising:

receiving, by the image analysis computing system, optical coherence tomography data (OCT data);

determining, by the image analysis computing system, an optical attenuation coefficient for each pixel of the OCT data to create optical attenuation coefficient data (OAC data) corresponding to the OCT data; and determining, by the image analysis computing system, an area exhibiting geographic atrophy based on the OAC data;

wherein determining the optical attenuation coefficient for each pixel of the OCT data to create OAC data corresponding to the OCT data includes calculating, for each pixel i, a value μ[i] that represents the OAC of the ith pixel, wherein:

$$\mu[i] = \frac{I[i]}{2\Delta \int_{i+1}^{\infty} I[i]}$$

wherein Δ is an axial size of each pixel;

wherein I[i] is a detected OCT signal intensity at the ith pixel; and wherein $$\int_{i+1}^{\infty} I[i]$$

is calculated by adding OCT signal intensities of all pixels beneath the ith pixel.

* * * * *